(12) United States Patent
Kurth et al.

(10) Patent No.: US 6,338,844 B1
(45) Date of Patent: Jan. 15, 2002

(54) GENOMIC NUCLEIC ACIDS, CDNA AND MRNA WHICH CODE FOR POLYPEPTIDES WITH IL-16 ACTIVITY, PROCESSES FOR THE PRODUCTION THEREOF AND THEIR USE

(75) Inventors: Reinhard Kurth, Dreieich; Michael Baier, Frankfurt; Norbert Bannert, Frankfurt; Karin Metzner, Frankfurt; Albrecht Werner, Weinheim, all of (DE)

(73) Assignee: Bundesrepublik Deutschland vertreten durch de Bundesminister für Gesundheit, Bonn (DE)

( * ) Notice: Subject to any disclaimer, the term of this patent is extended or adjusted under 35 U.S.C. 154(b) by 0 days.

(21) Appl. No.: 09/147,119

(22) PCT Filed: Apr. 9, 1997

(86) PCT No.: PCT/EP97/01753

§ 371 Date: May 11, 1999

§ 102(e) Date: May 11, 1999

(87) PCT Pub. No.: WO97/38105

PCT Pub. Date: Oct. 16, 1997

(30) Foreign Application Priority Data

Apr. 10, 1996 (DE) .......................... 196 14 099

(51) Int. Cl.[7] .................. A61K 38/20; C12N 15/09; C07K 1/00
(52) U.S. Cl. ................. 424/85.2; 536/23.1; 536/23.5; 536/24.3; 536/24.31; 435/69.5; 435/71.1; 435/71.2; 435/325; 514/2; 514/8; 514/12
(58) Field of Search ............... 536/23.1, 23.5, 536/24.3, 24.31; 435/69.5, 71.1, 71.2, 325, 471, 320.1, 252.3, 254.11; 514/2, 8, 12; 424/85.1, 85.2

(56) References Cited

FOREIGN PATENT DOCUMENTS

| EP | 0 736 600 | | 10/1996 |
| WO | WO 94/28134 | * | 8/1994 |

OTHER PUBLICATIONS

International Publication No. PCT/US94/05442, published Dec. 8, 1994.
International Publication No. PCT/EP96/05662, published Jul. 3, 1997.
Proceedings of the National Academy of Sciences of USA, vol. 91, May 1994, Cruikshant et al., "Molecular and Functional Analysis of a Lymphocyte Chemoattractment Factor".
Nature, vol. 378, Dec. 7, 1995, p. 563, Baier et al., "HIV Suppression by Interleukin–16".
Nature, vol. 381, May 2, 1996, p. 30, N. Bannert et al., "Interleukin–16 or not? reply to comments".
Nature, vol. 381, May 2, 1996, pp. 29–30, Bazan et al., "Interleukin–16 or not? reply to comments".
Journal of Allergy and Clinical Immunology, vol. 99, No. 1 part 02, Jan. 1997, p. S54, Mukhtar et al., "Identification of a full length human il–16 cDNA".
Proceedings of the National Academy of Sciences of USA, vo. 94, No. 10, May 13, 1997, pp. 5273–5277, Baier et al., "Molecular cloning, sequence, expression, and processing ...".
Doerks et al. 1998 Protein annotation: detective work for function prediction. Trends in Genetics. vol. 14, No. 6, pp. 248–250.*

* cited by examiner

*Primary Examiner*—Prema Mertz
*Assistant Examiner*—Sarada C Prasad
(74) *Attorney, Agent, or Firm*—Arent Fox Plotkin Kintner Kahn

(57) ABSTRACT

A nucleic acid with which expression of a polypeptide having interleukin-16 activity can be achieved or regulated in a prokaryotic or eukaryotic host cell, wherein in the region coding for the polypeptide, the nucleic acid (1) corresponds to the DNA sequence SEQ ID NOS:1 and 5–7 or its complementary strand; (b) hybridizes under stringent conditions with the DNA of sequence SEQ ID NOS:1 and 5–7; (c) or is a nucleic acid sequence which, if there was no degeneracy of the genetic code, would hybridize under stringent conditions with the nucleic acid sequences defined by (a) and (b); (d) and, if it codes for a polypeptide having interleukin-16 activity, is suitable as genomic DNA for the recombinant production of IL-16 in eukaryotic host cells and processes for producing the same and pharmaceutical compositions containing the same.

17 Claims, No Drawings

GENOMIC NUCLEIC ACIDS, CDNA AND MRNA WHICH CODE FOR POLYPEPTIDES WITH IL-16 ACTIVITY, PROCESSES FOR THE PRODUCTION THEREOF AND THEIR USE

The invention concerns regulatory elements of the expression of IL-16, genomic nucleic acids, cDNA and mRNA that code for polypeptides with IL-16 activity, processes for the production thereof and their use.

IL-16 (interleukin-16) is a lymphokine that is also denoted "lymphocyte chemoattracting factor" (LCF) or "immunodeficiency virus suppressing lymphokine" (ISL). IL-16 and its properties are described in WO 94/28134, the International Application PCT/EP96/01486 as well as by Cruikshank, W. W., et al., Proc. Natl. Acad. Sci. U.S.A. 91 (1994) 5109–5113 and Baier, M., et al., Nature 378 (1995) 563. The recombinant production of IL-16 is also described therein. According to this IL-16 is a protein with a molecular mass of 13,385 D. Cruikshank also found that ISL elutes as a multimeric form with a molecular weight of 50–60 or 55–60 kD in molecular sieve chromatography. The chemoattractant activity is attributed to this multimeric form which is a cationic homotetramer (product information AMS Biotechnology Ltd., Europe, Cat. No. 11177186). Baier describes a homodimeric form of IL-16 with a molecular weight of 28 kD. However, the chemoattractant activity described by Cruikshank et al., in J. Immunol. 146 (1991) 2928–2934 and the activity of recombinant human IL-16 described by Baier are very low.

The object of the present invention is to provide regulatory elements of IL-16 expression, to improve the activity of IL-16 and to provide forms of IL-16 which exhibit low immunogenicity and are advantageously suitable for therapeutic use.

The object of the invention is achieved by a nucleic acid with which expression of a polypeptide having interleukin-16 activity can be achieved or regulated in a eukaryotic host cell, wherein the said nucleic acid
a) corresponds to the DNA sequence SEQ ID NO:1 or its complementary strand;
b) hybridizes under stringent conditions with the DNA of sequence SEQ ID NO:1, preferably with nucleotides 1–6297 of SEQ ID NO:1;
c) or is a nucleic acid sequence which, if there was no degeneracy of the genetic code, would hybridize under stringent conditions with the nucleic acid sequences defined by a) or b),
d) and, if it codes for a polypeptide having IL-16 activity, has a length of at least 1179 coding nucleotides.

A preferred sequence is the cDNA sequence shown in SEQ ID NO:6, the complementary strand thereof or a sequence which under stringent conditions hybridizes with the sequence SEQ ID NO:6. SEQ ID NO:5 and the plasmid pCI/IL16 PROM also describe the genomic DNA of IL-16 and contain the introns and exons each parity or completely.

Such a nucleic acid preferably codes a polypeptide with IL-16 activity, particularly preferably the natural IL-16 of primates such as human IL-16 or IL-16 of a species of monkey or another mammal such as e.g. mouse.

It surprisingly turned out the FIG. 2 of WO 94/28134 does not describe the complete sequence of IL-16. The start codon "ATG" of the precursor form of the protein does not begin with nucleotide 783. The sequence has yet more differences to FIG. 2 of WO 94/28134. These are for example nucleotide substitutions (313 G by A, 717 C by A, 1070 G by T).

The sequence of IL-16 can differ to a certain extent from protein sequences coded by such DNA sequences. Such sequence variations can be amino acid substitutions, deletions or additions. However, the amino acid sequence of IL-16 is preferably at least 75% especially preferably at least 90% identical to the amino acid sequence of IL-16. Variants of parts of the amino acid sequence or nucleic acid sequence are for example described in the International Patent Application Nos. PCT/EP96/01486, PCT/EP96/05662 and PCT/EP96/05661.

Nucleic acids within the sense of the invention are for example understood as DNA, RNA and nucleic acid derivatives and analogues. Preferred nucleic acid analogues are those compounds in which the sugar phosphate backbone is replaced by other units such as e.g. amino acids. Such compounds are denoted PNA and are described in WO 92/20702. Since for example PNA-DNA bonds are stronger the DNA-DNA bonds the stringent conditions for PNA-DNA hybridization described in the following are not applicable. Suitable hybridization conditions are, however, described in WO 92/20703.

SEQ ID NO:6 describes the cDNA derived from the mRNA. The cDNA is suitable, for instance, for the determination of the corresponding RNA in tissue fluids and body fluids of mammals and humans. The cDNA is preferably used, however, for the expression of full length IL-16 in prokaryotes, preferably in $E.coli$. For that purpose the cDNA is inserted into an appropriate vector, transformed into a prokaryotic host cell, said host cell is cultivated, and, after cultivation, IL-16 is isolated. This can be done according to the methods known to one skilled in the art. If the protein is not secreted but obtained within the cell as a denatured insoluble protein (inclusion bodies), solubilisation and naturation must be carried out thereafter. These methods are also known to one skilled in the art.

SEQ ID NO:7 describes the amino acid sequence of IL-16 in its precursor form, which is also a subject matter of the invention.

The term "IL-16" within the sense of the invention is understood as a polypeptide with the activity of IL-16. IL-16 preferably exhibits the effect stated in the International Patent Application No. PCT/EP96/01486 or it stimulates cell division according to WO 94/28134.

IL-16 binds to $CD4^+$ lymphocytes and can suppress the replication of viruses such as for example HIV-1, HIV-2 and SIV. The function of IL-16 is not limited by its presentation in the MHC complex.

IL-16 in particular exhibits one or several of the following properties:
  binding to T cells via the CD4 receptor,
  stimulating the expression of the IL-2 receptor and/or HLA-DR antigen on $CD4^+$ lymphocytes,
  stimulating the proliferation of T helper cells in the presence of IL-2,
  suppressing the proliferation of T helper cells stimulated with anti-CD3 antibodies,
  suppressing the replication of viruses preferably HIV-1, HIV-2 or SIV.

The term "hybridizing under stringent conditions" means that two nucleic acid fragments hybridize with one another under standardized hybridization conditions as for example described in Sambrook et al., "Expression of cloned genes in $E.\ coli$" in Molecular Cloning: A laboratory manual (1989), Cold Spring Harbor Laboratory Press, New York, U.S.A. Such conditions are for example hybridization in 6.0×SSC at about 45° C. followed by a washing step at 2×SSC at 50° C.

To select the stringency, the salt concentration in the washing step can be selected for example between 2.0×SSC at 50° C. for low stringency and 0.2×SSC at 50° C. for high stringency. In addition the temperature in the washing step can be varied between room temperature ca. 22° C. for low stringency and 65° C. for high stringency.

A "regulatory element" is understood as a DNA sequence which regulates the expression of genes (e.g. promoter, attenuator, enhancer). A promoter is understood as a cis-acting DNA sequence which is usually 80–120 base pairs long and is located 5' upstream of the initiation site of the gene to be expressed. A promoter is in addition characterized in that RNA polymerase can bind to it and can initiate the correct transcription. A preferred DNA fragment with promoter activity spans nucleotides 2053–3195 of SEQ ID NO:1.

An enhancer is usually understood as a cis-acting DNA sequence of ca. 50–100 bp in length which is of paramount importance for an efficient transcription. Enhancer sequences work independently of orientation and position.

An intron is understood as a nucleotide sequence which is present in eukaryotic genes and is transcribed into pre-mRNA and is removed from the mRNA in a further step (splicing). The IL-16 gene contains several introns and exons which are described in SEQ ID NO:1, pCI/IL16 PROM and/or SEQ ID NO:5.

Plasmid pCI/IL-16 PROM contains a sequence upstream of SEQ ID NO:5. SEQ ID NO:5 describes the 3' terminal part of the genomic DNA whereas the plasmid describes the 5' terminal part. Both sequences overlap in the region of nucleotide 1 to nucleotide 87 of SEQ ID NO:5. Thus the plasmid contains the IL-16 sequence 5' upstream of nucleotide 87 of SEQ ID NO:5. These are coding sequences and regulatory elements as well as one or several introns. In the first intron of SEQ ID NO:5 about 600 base pairs are missing at the position denoted "N". These nucleotides can either be deleted or filled up by any nucleotides. However, it is important that the intron/exon junctions remain correct. The order of these base pairs is shown in SEQ ID NO:1.

A further subject matter of the invention are regulatory elements of the expression of IL-16 (in particular promoter and enhancer elements as they are present on the plasmid pCI/IL-16 PROM or in SEQ ID NO:1/SEQ ID NO:5 or can be derived therefrom). Promoter elements are at the 5' end upstream of exon 1. The enhancer elements are on the 5' side of the IL-16 gene to be expressed in the said plasmid as well as at the 3' end of SEQ ID NO:1/SEQ ID NO:5.

The regulatory elements according to the invention are particularly suitable for the expression of polypeptides with IL-16 activity in eukaryotic cells. The regulatory elements are, however, also suitable for expression of other genes in eukaryotic cells. The regulatory elements are particularly advantageous for expression in lymphocytes in particular in T lymphocytes and cells or cell lines derived therefrom. Suitable regulator sequences can be selected as described in example 7.

IL-16 is preferably recombinantly produced in eukaryotic host cells. Such production methods are known to a person skilled in the art and are for example described in EP-B 0 148 605. However, in order to obtain the forms of IL-16 according to the invention by recombinant production in a defined and reproducible manner, additional measures have to be taken beyond the processes for recombinant production familiar to a person skilled in the art. For this a DNA is firstly prepared which is able to produce a protein that has the activity of IL-16. The DNA is cloned into a vector that can be transferred into a host cell and can be replicated there.

Such a vector contains regulatory elements that are necessary to express the DNA sequence in addition to the IL-16 sequence. One or several regulatory elements contained in SEQ ID NO:1 are preferably used. Such a nucleic acid which contains the regulatory elements is transferred into a vector which is capable of expressing the DNA of IL-16. The host cell is cultured under conditions that are suitable for vector amplification and IL-16 is isolated. In this way suitable measures ensure that the protein can adopt an active tertiary structure in which it exhibits IL-16 properties.

A lymphoid expression cell line is preferably used instead of the usual host cells (COS, CHO). In this connection IL-16 may be processed into the active shortened form.

In this process it is not necessary that the expressed protein contains the exact IL-16 amino acid sequence from SEQ ID NO:7. Proteins are equally suitable which contain essentially the same sequence and have analogous properties. A eukaryotic expression using the regulatory elements and/or the genomic DNA of IL-16 ensures that IL-16 is correctly processed. In this way a protein is obtained in a recombinant manner which is essentially or completely identical to natural IL-16.

The nucleic acid sequence of the protein can be modified. Such modifications are for example:
- Modification of the nucleic acid in order to introduce various recognition sequences of restriction enzymes to facilitate the steps of ligation, cloning and mutagenesis
- modification of the nucleic acid to incorporate preferred codons for the host cell
- extension of the nucleic acid by additional operator elements in order to optimize the expression in the host cell.

In addition the expression vectors usually contain a selectable marker in order to select the transformed cells. Such selectable markers are for example the DHFR gene, the resistance genes for ampicillin, chloramphenicol, erythromycin, kanamycin, neomycin and tetracyclin (Davies et al., Ann. Rev. Microbiol. 32 (1978) 469). Selectable markers which are also suitable are the genes for substances that are essential for the biosynthesis of substances necessary for the cell such as e.g. histidine, tryptophan and leucine.

Further genetic engineering methods for the construction and expression of suitable vectors are described in J. Sambrook et al., Molecular Cloning: A laboratory manual (1989), Cold Spring Harbor Laboratory Press, New York, N.Y.

Recombinant IL-16 can be expressed in eukaryotic cells such as for example CHO cells, yeast or insect cells. CHO cells, COS cells or host cells derived from lymphocytes (preferably from T lymphocytes) are preferred as the eukaryotic expression system. Expression in yeast can be achieved by means of three types of yeast vectors: integrating $YI_P$ (yeast integrating plasmids) vectors, replicating $YR_P$ (yeast replicon plasmids) vectors and episomal $YE_P$ (yeast episomal plasmids) vectors. More details of this are for example described in S. M. Kingsman et al., Tibtech 5 (1987) 53–57).

A further subject matter of the invention is a eukaryotic host cell which is transformed or transfected with a nucleic acid that codes for an IL-16 polypeptide according to the invention in such a way that the host cell expresses the said polypeptide. Such a host cell usually contains a biological functional nucleic acid vector, preferably a DNA vector e.g. a plasmid DNA that contains this nucleic acid.

A further subject matter of the invention is human interleukin-16 or interleukin-16 from primates preferably human IL-16 which can be obtained essentially free of other human proteins as a correctly processed product of a eukaryotic expression. IL-16 is a protein that occurs as a monomer or as a multimer composed of monomeric IL-16 (denoted subunits in the following). The molecular weight of a monomeric IL-16 subunit is preferably ca. 14 kD. In addition a monomeric IL-16 polypeptide is preferred which cannot be cleaved into further subunits.

It surprisingly turned out that the nucleic acid and protein sequence of IL-16 described in WO 94/28134 do not correspond to the natural human sequences. This is merely an IL-16 fragment. However, for therapeutic use it is preferable to use a correctly processed protein which is either identical to the natural protein or only differs slightly from the natural protein and exhibits at least a comparable activity and hence low immunogenicity.

Within the sense of the invention the nucleic acid sequence of IL-16 can contain deletions, mutations and additions. An IL-16 (monomeric form, subunit) that is coded by such a nucleic acid can be multimerized in a preferred embodiment. In this way the activity of IL-16 can be increased. Such multimeric forms are preferably dimeric, tetrameric or octameric forms.

In a further preferred embodiment polypeptides of the invention can additionally contain a defined content of metal ions wherein the number of metal ions per subunit is preferably 0.5 to 2.

Within the sense of the invention many metal ions are suitable as the metal ions. Alkaline earth metals as well as elements of side groups have proven to be suitable. Particularly suitable are alkaline earth metals, cobalt, zinc, selenium, manganese, nickel, copper, iron, magnesium, potassium, molybdenum and silver. The ions can be monovalent, divalent, trivalent or quadrivalent. Particularly preferred are divalent ions. The ions are preferably added as solutions of $MgCl_2$, $CaCl_2$, $MnCl_2$, $BaCl_2$, $LiCl_2$, $Sr(NO_3)_2$, $Na_2MoO_4$, $AgCl_2$.

Such multimeric forms and forms of IL-16 containing metal ions are described in the International Patent Application No. PCT/EP96/05661.

The polypeptide according to the invention can be produced in such a way that a eukaryotic host cell which is transformed or transfected with a nucleic acid according to the invention is cultured under suitable nutrient conditions and the desired polypeptide is optionally isolated. If the polypeptide is to be produced in vivo as part of a gene therapy treatment, the polypeptide is of course not isolated from the cell.

In addition the invention concerns a pharmaceutical composition which contains a polypeptide according to the invention in an adequate amount and/or specific activity for a therapeutic application as well as optionally a pharmaceutical suitable diluent, adjuvant and/or carrier.

The polypeptides according to the invention are particularly suitable for the treatment of pathological states that have been caused by viral replication especially retroviral replication and for immunomodulation. Such therapeutic applications are also described in WO 94/28134 as well as in the International Patent Application No. PCT/EP96/01486. Diagnostic test procedures are also described in the latter.

The polypeptides according to the invention can preferably be used for immunosuppression. This immunosuppression is preferably achieved by inhibiting the helper function of $TH_O$ and/or $TH_1$ and $TH_2$ cells. The polypeptides according to the invention are therefore of therapeutic value in all diseases in which an immunodys-regulatory component is postulated in the pathogenesis, in particular a hyperimmunity. Diseases which can be treated with IL-16 can be diseases in cardiology/angiology such as myocarditis, endocarditis and pericarditis, in pulmonology these are for example bronchitis, asthma, in hematology autoimmune neuropenia and graft rejection, in gastroenterology chronic gastritis, in endocrinology diabetes mellitus type I, in nephrology glomerulonephritis, diseases in the field of rheumatoid diseases, diseases in opthalmology, in neurology such as multiple sclerosis, in dermatology such as eczema. The polypeptides according to the invention can in particular be used in autoimmune disease, allergies and to avoid graft rejections.

A further subject matter of the invention is the use of nucleic acids according to the invention in the field of gene therapy. Vector systems that are suitable for this are for example retroviral or non-viral vector systems.

The following examples and publications as well as the sequence protocol are intended to elucidate the invention, the scope of which is characterized by the patent claims. The methods described are to be understood as examples which also after modifications still describe the subject matter of the invention.

The plasmid pCI/IL 16 PROM was deposited on the 26.03.96 under the No. DSM 10603 at the "Deutsche Sammlung von Mikroorganismen und Zellkulturen GmbH (DSM)", Mascheroder Weg 1b, D-38124 Braunschweig.

General

Cells

Human peripheral blood mononuclear cells (PBMC) were isolated by Ficoll Hypaque gradient centrifugation and cultivated in RPM 1640 medium supplemented with 20% fetal calf serum, 100 units/ml IL-2 and 5 µg/ml phytohemagglutinin (PHA). T lymphocyte subsets were prepared as described by Ennen, J., et al., Proc. Natl. Acad. Sci. U.S.A. 91 (1994) 7207–7211.

RNA preparations and Northern blotting

Total RNA was extracted using the RNA-Isolation Kit (Stratagene, La Jolla, U.S.). Poly ($A^+$) RNA was isolated from total RNA with the Oligotex-dT mRNA system (Qiagen, Hilden, DE). 10 µg of total RNA or 2 µg of Poly ($A^+$) RNA were loaded on a formaldehyde agarose gel and after electrophoresis blotted onto a positively charged nylon membrane (Boehringer Mannheim GmbH, DE). The IL-16 cDNA probe was generated using the PCR DIG-probe synthesis system (Boehringer Mannheim GmbH, DE) and spans the IL-16 cDNA region from nucleotide 1693 to the end of the reading frame at nucleotide 2082. Hybridizations were carried out at 58° C. overnight followed by several high stringency washes. For detection of the signals the DIG luminescent system (Boehringer Mannheim GmbH, DE) was employed according to the manufacturer's recommendations. The quality of RNA preparations was routinely assessed by hybridization with a 13-actin probe. The Human RNA master blot (Clontech Laboratories, Palo Alto, U.S.) was analysed with the same IL-16 cDNA hybridization probe under comparable conditions.

Reverse transcription and PCR

Identification of the 5' end of IL-16 precursor mRNA was performed using the 5' RACE system for rapid amplification of cDNA ends (Life Technologies, Gaithersburg, U.S.). Additional RACE experiments were carried out with parts of the CapFinder system and Marathon-Ready cDNAs from human lymph nodes, leukocytes and murine leukocytes respectively (all from Clontech Laboratories, Palo Alto, U.S.). All other cDNAs were synthesized using up to 5 µg of total PBMC RNA and oligo-dT as primer (Pharmacia, Uppsala, SE).

Gel purified PCR products were ligated into the pGEM-T vector (Promega, Madison, U.S.) before determination of the nucleotide sequences according to standard methods.

Peptides and antibodies

Antibodies specific for pro-IL-16 coupled to KLH via disulfide bonds were raised in rabbits. The antisera and the peptides were obtained from the Custom peptide antibody production program (Eurogentec, Seraing, BE). Recombinant IL-16 (rIL-16His) was used to raise antisera in goats (Baier, M., et al., Nature 378 (1995) 563). Affinity purified goat anti-IL-16 antibodies were used at an IgG concentration of 0.25 µg/ml in immunoblot experiments.

Immunoblots

Cell lysates were prepared by incubation of $2.5 \times 10^7$ cells in 400 µl of solubilization buffer (20 mM Tris HCl, pH 7.5, 1% NP-40, 150 mM NaCl, 5 mM EDTA, 1 mM phenylmethyl-sulfonyl-fluoride, 10 mM sodium fluoride, 1 mM sodium pyrophosphate, 5 µg/ml aprotinin and 5 µg/ml leupeptin) for 15 minutes on ice. Nuclei were removed by centrifugation and the volume was finally adjusted to 500 µl with 4×SDS sample buffer. Immunoblots were carried out according to standard protocols. Antisera were used at appropriate dilutions in blocking buffer (phosphate buffered saline (PBS), pH 7.2, 5% Marvel). Finally, bound antibody was detected using the enhanced chemoluminescence (ECL) kit (Amersham, Little Chalfont, UK).

Proteolytic cleavage of pro-IL-16 in cell lysates

Purified CD8(+) cells were lysed after cultivation for 2 days by incubation in PBS-Dulbecco/1% NP-40 for 10 minutes on ice. Lysates were clarified by centrifugation and finally diluted 1:5 in PBS. The equivalent of $4.5 \times 10^6$ cells was incubated with 30 µg rIL-16His in a volume of 66 µl for 1648 hours at room temperature. Thereafter, the cleavage of rIL-16His was analysed by immunoblotting with 1:100 diluted serum 802, which recognizes the carboxyterminus of IL-16.

Example 1

A 2.6 kb mRNA is the main IL-16 transcript and is predominantly expressed in lymphatic tissues.

IL-16 mRNA expression in PBMC was examined by Northern blotting using a fragment corresponding to the carboxyterminal 390 bp as hybridization probe under stringent conditions. The major transcript in PBMCs is of 2.6 kb length.

The human RNA tissue blot allows the direct quantitative comparison of gene expression in 50 different tissues. IL-16 mRNA was detectable at equally strong levels in spleen, thymus and lymph node samples. Significantly lower levels of expression were seen in peripheral leukocytes, bone marrow, fetal spleen, fetal thymus, stomach and the cerebellum. Only traces of IL-16 specific mRNA were found in appendix, occipital lobe, salivary gland and mammary gland tissue. Thus, 13 out of 50 tissues scored positively in this hybridization analysis. From the 13 positive tissue samples 8 were of lymphatic origin including those with the highest expression levels.

Example 2

Identification of the IL-16 mRNA 5' end by different RACE approaches

To confirm that the IL-16 precursor mRNA is indeed larger than previously described, 5' RACE experiments were conducted using an oligonucleotide located in a known region of pro-IL-16 as primer for the cDNA synthesis. The cDNAs were tailed by use of the terminal deoxynucleotidyl transferase and finally amplified with PCR primers specific for IL-16 and the homopolymeric dC-tail. To enhance the specificity of these PCR amplifications in some cases secondary nested or semi-nested PCRs prior to cloning the products were performed, Surprisingly, the IL-16 cDNA sequence extends almost 1 kb beyond its previously published 5' end. The CapFinder system displays higher selectivity for reverse transcripts of complete mRNAs (Zhu, Y., et al., Clontechniques 11 (1996) 30–31) and was therefore used in combination with IL-16 specific primers for cDNA synthesis to extend and confirm the sequence information obtained with the tailing approach. With both methods the 5' end of the pro-IL-16 cDNA was found to consist of a fairly heterogenous set of transcriptional starting points. Similar results were obtained with commercially available cDNAs from human lymph nodes, leukocytes and murine leukocytes respectively. Incompletely processed transcripts were also found containing parts of an intron just upstream of the putative initiation codon.

Example 3

Sequence of the IL-16 precursor

The complete nucleotide and deduced amino acid sequence of the pro-IL-16 cDNA is shown in SEQ ID NO:6. The first ATG is found at position 190 and if used as a start codon would result in a relatively hydrophylic protein of 631 amino acids with a calculated molecular weight of 67 kDa. Use of the second ATG at position 271, which is in frame and in very good context for the initiation of translation, would give rise to a 63 kDA protein. The putative 5' leader sequence is G-C rich (61%) and may contribute to the formation of secondary structures.

The most significant homologies in database searches were seen to the presynaptic density protein 95 and the tight junction protein ZO-1 (Genbank accession numbers P31016 and Q07157 respectively). Both carry GLGF motifs and the resemblance is solely due to the three GLGF domains in the carboxyterminal half of the pro-IL-16 sequence.

Database searches for the 3' untranslated region (UTR) of the pro-IL-16 cDNA, which has a proposed length of 979 bp, were also carried out. The three expressed sequence tags (Genbank accession numbers N38840, H57532 and N22522) that cover the 3' end were found to begin in a region between nucleotides 2371 and 2385 due to utilization of the polyadenylation signal at nucleotide position 2353. Thus, for the majority of transcripts the 3' UTR of approximately 303 nucleotides would be significantly shorter than previously described.

Example 4

Immunoblot detection of pro-IL-16 in cell lysates

The IL-16 precursor protein was detectable in mitogen stimulated PBMCs as a protein band with an apparent molecular weight of about 80 kDa. In freshly isolated as well as in serotonin stimulated cells an almost equally strong second 60 kDa band was seen. Only overexposure of films allowed detection of the same 60 kDa protein in the samples after 2 days of cultivation in the presence of mitogen and IL-2.

To verify that the pro-IL-16 cDNA can be expressed the pro-IL-16 coding region under transcriptional control of the CMV promoter (pcDNA3, Invitrogen, San Diego, U.S.) was transfected into COS-7 cells. Immunoblots with lysates from transfected cells and PBMCs revealed that transfected cells, but not untransfected controls, express an 80 kDa protein which migrates in a manner identical to the pro-IL-16 found in PBMCs. Similar results were seen with pro-IL-16 specific serum 804 whereas use of pre-immunization sera gave no signals.

Example 5
Proteolytic cleavage of pro-IL-16 in cell lysates

The IL-16 precursor protein should be a substrate for proteases present in or on CD8(+) cells, the action of which would release the biologically active carboxyterminal portion. A recombinant pro-IL-16 fragment of 39 kDa is specifically proteolytically processed upon incubation in CD8 (+) cell lysates and not in lysates from CD4(+) cells. It was investigated whether the recombinant 130 aa fragment would still act as a substrate for this proteolytic activity. Indeed, incubation of rIL-16His, which migrates as a 19 kDa protein in SDS gels, with CD8(+) cell lysate yields the same 17 kDa carboxyterminal fragment as seen previously in the 39 kDa precursor variant cleavage assays. No protease activity is detectable during the incubation time without addition of cell lysate. Therefore it is likely that naturally processed IL-16 is smaller than the originally suggested 130 amino acids. Preliminary laser desorption mass spectroscopy data obtained with purified cleavage products indicate that proteolytic processing occurs at the aspartate residue 510.

Example 6
Construction of the plasmid pCI/IL 16 PROM

A DNA fragment which contains the putative IL-16 promoter and further regulatory elements was amplified using the promoter Finder™ DNA Walking Kit (Clontech-laboratories, Palo Alto, Cat.# K1803-1). The kit mentioned above contains 5 DNA libraries with adaptor-ligated human subgenomic fragments. A ca. 2.7 kb large fragment was amplified in a nested PCR with 1 µl DNA from the Ssp I library as a template. In the first PCR cycle the adaptor primer AP1 from the kit and the gene-specific primer GSP1 were used. In the second cycle the adaptor primer AP2 from the kit and the gene-specific primer GSP2 were used. The gene-specific primer are reverse and complementary to sequences from Exon 2 according to SEQ ID NO:1.

Sequence of the primer GSP1:

(SEQ ID NO:2) CTTTTCGTCAAGTAGCTTCGTCT-CACAG

Sequence of the primer GSP2:

(SEQ ID NO:3) GAAATCGAAGCGGCCGCGCTC-CGTGCTCGCTGGCTAGGCATCTTGAG

The amplificates were digested with the restriction endo-nucleases Mu I and Not I and cloned into the expression vector pCI (Promega Corporation, Madison, Cat.# E1731). The constructed plasmid pCI/IL 16 PROM (DSM 10603) is ca. 6.7 kb in size. Due to the design of the Promoter Finder kit the following nucleotides of the Promoter Finder adaptor are present in front of the 5' end of the cloned subgenomic sequence: (SEQ ID NO:4) GGTCGACGGC-CCGGGCTGGT.

Example 7
Selection of IL-16 regulator sequences

In order to determine whether a promoter sequence is present in SEQ ID NO:1 DNA fragments upstream of Exon I were cloned in front of a reporter gene (e.g., luciferase, de Wet, J. R., et al., Mol. Cell. Biol. 7 (1987) 725–737). When such a fragment exhibits promoter activity, there is an expression of the reporter protein which can be detected by standard methods (Luciferase Assay system from Promega, Cat.# E1500). Promoter activity was identified in a fragment spanning nucleotides 2053–3195 according to SEQ ID NO:1.

Example 8
Expression, purification of recombinant human IL-16

CHO cells are transformed, selected, fermented and lysed using an expression plasmid which contains the genomic IL-16 gene according to SEQ ID NO:1 or the (mRNA analogous) cDNA sequence SEQ ID NO:6.

After centrifugation the supernatant is applied to a Q-Sepharose FF column (45 ml; Pharmacia) which has previously been equilibrated with 20 mM imidazole, pH 6.5. IL-16 is eluted with a gradient of 0 to 0.3 M NaCl in 20 mM imidazole, pH 6.5. Fractions containing IL-16 were identified by means of SDS-PAGE and pooled. The identity of IL-16 was confirmed by mass analysis and automated N-terminal sequence analysis. In order to determined the concentration the UV absorption of IL-16 at 280 nm and a calculated molar absorption coefficient of 5540 $M^{-1}$ $cm^{-1}$ at this wavelength (Mack et al. (1992) Analyt. Biochem. 200, 74–80) are used.

The IL-16 obtained in this way had a purity of more than 95% in a SDS-PAGE under reducing conditions. The analytical Superdex 75 FPLC column (Pharmacia) was eluted with mM Na-phosphate, 0.5 M NaCl, 10% glycerol, pH 7.0 and a flow rate of 1 ml/min. The amount of protein applied in a volume of 100 to 150 µl was 1.5 to 15 µg protein. The detection was at 220 mn.

A Vydac, Protein & Peptide C18, 4×180 mm column is used for the purity analysis by means of RP-HPLC. It was eluted by a linear gradient of 0% to 80% B (solvent B: 90% acetonitrile in 0.1% TFA; solvent A: 0.1% TFA in $H_2O$) within 30 min. at a flow rate of 1 ml/min. It was detected at 220 nm.

LIST OF REFERENCES

Baier, M., et al., Nature 378 (1995) 563

Cruikshank, W. W., et al., J. Immunol. 146 (1991) 2928–2934

Cruikshank, W. W., et al., Proc. Natl. Acad. Sci. U.S.A. 91 (1994) 5109–5113

Davies et al., Ann. Rev. Microbiol. 32 (1978) 469 deWet, J. R. et al., Mol. Cell. Biol. 7 (1987) 725–737

Ennen, J., et al., Proc. Natl. Acad. Sci. U.S.A. 91 (1994) 7207–7211

European Patent No. 0 148 605

Patent Application No. PCT/EP96/01486

International Patent Application No. PCT/EP96/05661

International Patent Application No. PCT/EP96/05662

Kingsman, S. M., et al, Tibtech 5 (1987) 53–57

Mack et al., Analyt. Biochem. 200 (1992) 74–80

Sambrook et al., "Expression of cloned genes in *E. coli*" in Molecular Cloning: A laboratory manual (1989), Cold Spring Harbor Laboratory Press, New York, U.S.A.

WO 92/20702

WO 92/20703

WO 94/28134

Zhu, Y., et al., Clontechniques 11 (1996) 30–31

What is claimed is:

1. An isolated nucleic acid encoding a polypeptide with interleukin-16 activity, comprising a nucleic acid sequence selected from the group consisting of
   (1) at least nucleotide sequence 2053 to 3195 of SEQ ID NO: 1;
   (2) the nucleic acid sequence of SEQ ID NO: 5;
   (3) the nucleic acid sequence of SEQ ID NO: 6; and
   (4) a nucleic acid sequence which encodes the amino acid sequence of SEQ ID NO: 7.

2. A process for producing a polypeptide with interleukin-16 activity, comprising
   (a) transforming or transfecting a host cell with a nuclei acid according to claim 1, to obtain a transformed or transfected host cell;
   (b) culturing the transformed or transfected host cell to obtain a cell culture;
   (c) expressing the nucleic acid in the transformed or transfected host cell to produce the polypeptide; and
   (d) isolating the polypeptide from the cell culture.

3. The process of claim 2, wherein the host cell is a prokaryotic cell.

4. The process of claim 2, wherein the host cell is a eukaryotic cell.

5. A process for producing a polypeptide with interleukin-16 activity, comprising
   (a) providing a vector containing a nucleic acid according to claim 1 and regulatory elements necessary to express the nucleic acid in a eukaryotic host cell;
   (b) transforming or transfecting a eukaryotic cell with the vector to obtain a transformed or transfected host cell;
   (c) culturing the transformed or transfected host cell to obtain a cell culture;
   (d) expressing the nucleic acid in the transformed or transfected host cell to produce the polypeptide; and
   (e) isolating the polypeptide from the cell culture.

6. A host cell which is transformed or transfected with a nucleic acid according to claim 1, wherein the host cell expresses the polypeptide with interleukin-16 activity.

7. The host cell of claim 6, wherein the host cell is a prokaryotic cell.

8. The host cell of claim 6, wherein the host cell is a eukaryotic cell.

9. A vector containing a nucleic acid according to claim 1.

10. A polypeptide with interleukin-16 activity, wherein the polypeptide can be expressed using a nucleic acid according to claim 1, wherein the polypeptide has a molecular weight of about 14 kD.

11. A multimeric polypeptide with interleukin-16 activity, wherein the multimeric polypeptide is composed of a plurality of subunits, and wherein the subunits comprise a polypeptide according to claim 10.

12. The multimeric polypeptide of claim 11, wherein the multimeric polypeptide is composed of two, four or eight subunits.

13. A complementary nucleic acid of the nucleic acid of claim 1.

14. A pharmaceutical composition, comprising a nucleic acid according to claim 1, in combination with a pharmaceutically acceptable carrier.

15. An isolated nucleic acid which can hybridize with the nucleic acid of claim 1, at hybridization conditions selected from the group consisting of:
   (a) low stringency hybridization conditions characterized by a hybridizing step in 6.0×SSC at about 45° C. followed by a washing step in 2.0×SSC at 22–50° C.; and
   (b) high stringency hybridization conditions characterized by a hybridizing step in 6.0×SSC at about 45° C. followed by a washing step at 0.2×SSC at 50–65° C. wherein the isolated nucleic acid encodes for a polypeptide having a length of 631 amino acids similar or equal to the sequence of SEQ ID NO: 7.

16. An isolated nucleic acid which can hybridize with the nucleic acid of claim 1, at hybridization conditions selected from the group consisting of:
   (a) low stringency hybridization conditions characterized by a hybridizing step in 6.0×SSC at about 45° C. followed by a washing step in 2.0×SSC at 22–50° C.; and
   (b) high stringency hybridization conditions characterized by a hybridizing step in 6.0×SSC at about 45° C. followed by a washing step at 0.2×SSC at 50–65° C. wherein the isolated nucleic acid consists of 7 exons and 6 introns.

17. An isolated nucleic acid which can hybridize with the nucleic acid of claim 1, at hybridization conditions selected from the group consisting of:
   (a) low stringency hybridization conditions characterized by a hybridizing step in 6.0×SSC at about 45° C. followed by a washing step in 2.0×SSC at 22–50° C.; and
   (b) high stringency hybridization conditions characterized by a hybridizing step in 6.0×SSC at about 45° C. followed by a washing step at 0.2×SSC at 50–65° C. wherein the isolated nucleic acid contains the intron/exon junctions according to SEQ ID NO: 1.

* * * * *

SEQUENCE LISTING (1) GENERAL INFORMATION:

(iii) NUMBER OF SEQUENCES: 7

(2) INFORMATION FOR SEQ ID NO: 1:

(i) SEQUENCE CHARACTERISTICS:
      (A) LENGTH: 15936 base pairs
      (B) TYPE: nucleic acid
      (C) STRANDEDNESS: double
      (D) TOPOLOGY: linear (ii) MOLECULE TYPE: DNA (ix) FEATURE:
      (A) NAME/KEY: exon
      (B) LOCATION:3100..3238

(ix) FEATURE:
      (A) NAME/KEY: exon
      (B) LOCATION:5540..6635

(ix) FEATURE:
      (A) NAME/KEY: exon
      (B) LOCATION:7504..7672

(ix) FEATURE:
      (A) NAME/KEY: exon
      (B) LOCATION:9711..9812

(ix) FEATURE:
      (A) NAME/KEY: exon
      (B) LOCATION:12065..12323

(ix) FEATURE:
      (A) NAME/KEY: exon
      (B) LOCATION:12578..12703

(ix) FEATURE:
      (A) NAME/KEY: exon
      (B) LOCATION:14767..15936

(xi) SEQUENCE DESCRIPTION: SEQ ID NO: 1:

```
CTGGTACTTT CATGTACATT GTGTCAATTA AATCTTACAA CCACCTGATG GTGAGAGTCC     60

CAGTTGTGCA AAGAGGGAAC TGAGAAACTC GCTCAAGTTC ACATTGCTAG TGGGTCACAG    120

TTACCCACTA TGCAATGCTG AGTTTCCCAT CCTTACCCAG AAGCTGTCTC CCCCATCACG    180

GAATGGCCCT GCAGGGCCT TGGCCCTTCC CTTAAGCACA CCGTGGGCAG GTGGGAGGGG     240

GCCTCTGGAA ATCCCCTAAA ACAATCTACA GTGAGGGTTG GCAAGCTTCA GGAGGGGTAG    300

CGGTGGAGAC GGGATGTTGA GTAGGAGGGG TGAAAGTGAA GGAGGGAGGA GGAAGTCAGG    360

TTACTAAAAA GGAAGTGCAG TTTTGCAGAG CGCTGGCAGG ATGTGGCTGG TTAGCAACAC    420

ATGATGGAGT TATCAGATGG ATCTGTTCTC CCACCCCCTC TTTTAAGCCC ATATTTCATT    480

TTCCCTTGGG CCTGAGACCT ATGAGTCCAG AAGGGCAAAT CAGGAGCAGC CAGCTGAGAA    540

GCCAGTCATT TTGCCTTCCT CCTGGAGGCC CAGAAAAGGA GTGCAGTTGC CACAGCAGGT    600

CTGTCCCAGT GATGCCCTTG GCAGAGCCAC ATAGGGTCAG GGAATATTCC CGAGTAAGGC    660

GTCTGGAGAA GGAACTGGGG TGTCCTCAGG GAAGCCCAGG CAAGGAACTT CCCACAGGTC    720

ATCTTTCATG CCCTGTGTGC CTCAGCAGAA TACAGGGCTC CCTCCTGTAC CTGCCCCCAA    780

CAGCACCGTC TCCTGGAGAC AAGGCCGTTC TGCAGCTGCC CTCCTCTGTT TGCTCTGGTC    840

TGTCCCACGT GGCCAGCAGA TCCTTCTCCC ACAAACATTT CCATAAAAGC AATCAGCACG    900

ACATAATTTT ATTGGGCACT GGAGAGGCGG GGGTCACAGA GAAAGGATCA TAGCACGCAA    960
```

-continued

```
TAGAAAACAG GAAGCAATTT GCTTGAGGTC ACTCTCAAAA TTTCCTTGAC CATTCCTGGG   1020
GATTTCTCAC TGGATGTTTT CTTCCGTGGC CACAGTGTCC ACTGTCTCAC TCTCCCACTT   1080
TTCCCTCCCT GCAGTCTTTT CTCTACAGGG TCCCAAGACT GTTGTCAAGC TGCTATGGAT   1140
GACCCCCAAG TCTTTCCCAT CTACTCTAAT TCAAGGGGAC TTAACTCTCA CAACCAATAT   1200
GAACTTTGGG ATATTTTCTT CAACAAAAAA CTAACATCCC TCTTATAAAA AATCAGCCTA   1260
AACTCTCCCC CGTGCTTTAA AAAACTTGCT TAAAAAAACA CAACAGGATT TTCGAAGAAT   1320
CCTTTCTTAG AAAACAAACA AAAAACCAAA CAAAAACGTA CTTTCTCCCC ACTATGCTGA   1380
ATCTGCTCTC TCCCTCTTTC CTTCTTTCTC TTCTCCCTCC CTCATCCACC AAGCATGGTT   1440
CCAGGAAACA CTAGTAAGAG AAAAATTTGT GTAAAATCAA ATTTATTTCA GGGGCTAATT   1500
CTGAAGTCTC CCATGAAGAG GATGCAATAT TGGATGTGTT GATGAAAAGA CAAAACACAT   1560
TTGTGCTGTT CTAAGTTGTA AAGCTGCATT GACTGCAGTT GGTATCACAT GTGGCTGCCT   1620
GTAAAAGAGC TAACAATCCA TGAATGTCAA CAGATGTCAA CTTACAGAGC TCCCAACCAG   1680
GTGAAATTAA ATTTCATCCC CATGTAATTT CTCTTGTGGA CAAGAGACTT AGAGATCATC   1740
AGGCCAATAT TTGGAGCTTC TAATGCCATG ACTCAGCCTT ACTTTTTTTA AGGGCTAGTT   1800
CGAGAAGCTC AATGATTCCT TTGAAATTGG TTGATCTCTC AGTATTTCAT AATGCTCTCC   1860
TAAAGCTCAG TTCTACAGTA GGGAACTCGA GCTGAGGCAA TGCTCTGTGA ATACACTTCT   1920
AACTTTTGTA GACCTTTGCT TCCTCCAAAA TGTTTATTGT CAATGTAGAT CTTAAATTTC   1980
AGGTCATGGA TATTTGCCAT TGCTTTTTTA GTCCCAAAGG ATGCATTTGT TCCTTCCTCT   2040
TTCCTTCCTC TCTGGAAGGA AGCCTGCAGC CATGTCAAAT GGCCCATCAT TACACAAATC   2100
TGGAATGAAC CGGACGTGGA GGCCACCGCA GTATAGCAAA GCATTTCTCT TGCAGACAAT   2160
CAAATACAGG TGGCATCATT TTGATGATGT CTGCTTTCTC AATCTTTTTT TCCAGATGGG   2220
TATTATGTTT GGTTGGGCTA TGTCTCTGGA ACACTATTTT TCTGCCTCTC TGCCTGCAAA   2280
ATTCTTACTC TGTTTATGAA GCAGACAGAA AGTACTTCTC TAGGAAGCCT TCTCCACCTC   2340
TGGGATGGAA CTGGTCTCTC TGTTTCCTCT GGGCCCTGAC AGTACCTTAA GCACACTGTG   2400
TGATAATCCA AACTCTTCAA GTATTGCATA GCTATTCAGA GCCTGGTTCA TCTTGTCCCT   2460
AGGCTGTTTT GGGAGGACCC CAAGGCTGCA TCCAGGCTCA GTGGTGGAAA CAATTCTGCA   2520
ACAGATTGAG GATGTCACCC TAGGTGCCAC AGAGGGGAGC AATGGCACAG GTGCTGAGTA   2580
TCTGTCATCT TTTGCAGAAC ACTTACTAAA TATTTGAAGA GTGCTTAACA AGTGACAGCA   2640
ATTGACAAGC ATTTTCCTGA GTGCTCTAAC CTTAGGGAAC ACTAGCTGCC AGGTTTTTTT   2700
GCTGCCTTGT TTCTACGCTG CCCTATACCC TCCCGGGGTG GGTAGTTCAC CAGATGCAGT   2760
TGTAACTGAA GCAATGCCAG TCCCTCCACA CTCAAAGCCT TTTGTTCCTA TCATAAAGAG   2820
TCAGGGTCTT CAAGTATGTC AACAGTATGA GCCCATGACC TGGATACCAG GTTGCTGGAA   2880
GTCAAGGGGT GCTCTGCATG TCTAGGAGGT GCTGGCTCTG CCACGTCAGC ACCAAGGAGA   2940
AAAGAATCCT CTTTACATGG CTGCTGATGA ACTTCTCACT GAAAGCAGCT CAATATCCGT   3000
TTTTCCGTCC CAATCAAAGC GTGTCTCGCC TTCTCACAGC TTGAGGCTAC CGTTTTGACA   3060
TGGTCTCGCT TCCTGTTTAC ACCACAGGAA GCGAGAGAGC TGCTGCCACT GCTGCTACCA   3120
CAGGAAGACA CAGCAGGGAG AAGCCCTAGT GCCTCTGCCG GCTGCCCAGG ACCTGGTATC   3180
GGCCCACAGA CCAAGTCCTC CACAGAGGGC GAGCCAGGGT GGAGAAGAGC CAGCCCAGGT   3240
AAGCTTTCAT TGAGATCTTC CAAAAGAAAG GGTCTTTTGA AAAAAGGTGC AGGGATAAGA   3300
```

-continued

```
TAAGAGCACA AATTGGCCTG AGGATCAGAG TGCTCTGCTT TGACATCACC ACTGGACCTG   3360

GCTGATCAAC AGTCAAGGGT TCCAGGTGCT GGGCAGCAGC ACCGTGGAGG TGCTGTCCAG   3420

GGTGGGGAGC CTCCTGGGTG GACGGGTGAT GCTGTGGGGG TGGCAGCAGG AATGCAGGCC   3480

ATTCTGGATA ATTGGGAGGA TGGAGCCCTT GGAAGAGGTC CAAAGACACA CCCACCCAGC   3540

CATCCTGGGC AGCTACCTCT AGGGTGCCAA CATTCCAGTT GCAACAGTCC TGCTGCATTC   3600

AGGATTTCTG AGTCAGAGAA TGCAACGCCA GAAAAGTATA AATAGCATCT ACCAGTGGTC   3660

ACCTCCTCCA TGAGGTGGAT AGCAAGGGTG TGTCCACATG GTACACCTGA CAATGCTAAG   3720

ACATGACTTG AATATTTATT TGCTTGCTAG AGAGAGCATA GGACTTGAAG TCAGGGAATC   3780

CTGGATCTGT CTGTCATTAG TATGATTCTG AGCAACCTAC TTTGCCTTTC TGAGCCCAGA   3840

TTCACTCATC AGCAATGTGT GGAAGAGCAC GTAGACCCCA AGCATATGAT GCATTCAGCA   3900

AGCACACATT GAATGCTGGC TTCGTGAGGC CCTGTGCTAG GTGCTGGGGG GAGAGAGAGA   3960

AAGGGATGAG ACCAGGTAGT CAGGTCCTGC CTCCAAGGAG CAACTAGTAG TGGCAGGAAA   4020

TAAACATATA GACTATAAAA CATATGACTG TTTGAGTAAC ACTACAGAAA AGCTCATGAA   4080

AGACTTTTGG AGGGCTAAGG GACATTTTGG AAAGATCTAG CACATCTCAC CCAGAGCAGA   4140

GGCCCTGTGG GTGGAGGCTC CTCTCCCTTA GTCACCCTAA TTGAGGAACA TTCTAGCAAA   4200

AGCAAACGCC TCAGTGTTTA ACTGACAGGA GGTTGTCACT CCAATCTGCA AAGGGCTTGC   4260

CTGTGGAACT TCTGCCTCCT GATTCTCACA ACAGCACCTT ACAGCCAAGC CATTCAAAAA   4320

TGCAGAAACA GGCTGGAGGC CTGGGCTCAC TTGCCCAAGG CCAGTCTCTT AGATTGTGCA   4380

GAATTTCTCT TTGATATCAT CAAGGTGTAA TGCTCCATGA TTCACTTCTT TTGAAACCTG   4440

GCATTGAGAC AAGGGACAGG AGGGATCAGA GTTCCTTCAA CTGGGTTGCG TTCCAGTAGC   4500

AAGCATCCCC CAAGGCACAC AGGCCAGCCT CCCTCTGCCC CTGGGAAAGA GACCAGGACA   4560

CCCTCTCCCT TTACCCATGC AGACATGATG CTGGTTCAAT GCTGGCTTCT GAGAAAGACT   4620

CCTATGTGCT CCAGGGCATG CCTGAGGTCC TGGCTGGCAC AGAGCAGGTT GCACATTGCA   4680

ATCCCCTGCT CATCACATTC CCAACACTCA GGTTGCATCC CAGGTATCTT CAGTCAGTAC   4740

CTAGGGGTGG GCGTCAGTAT TTTTCAGGGC CCTCCAGATT CCAGTATGTA GCCAAGGTGG   4800

AGAATCCTAC TTCACAGATT CCTTTCTACC TGGAACCTTT TCATCAGCTT TTGAGGGAGG   4860

GAAAACACTC CTTTGCCGAG GGCAAGCTGA TCAATGACCT GTGTATAGGC AGAGCAGCAA   4920

ACACACGGCT TCAGGCCAG GCAGGTACAT ACATGGGAAA TGCTGGCTGG GTGAGAGGGA   4980

GCGTGAAGAG CTGTGGGAAG CCGAAGTGGC CCCATCAGAA GCTGTGCACA GGCACCTTGT   5040

TTTTAATGAC ACGGGTAGGT CAAAGCACAA ACAGCTGCCA ACTCATGACC TTTGTCTTAA   5100

AAGTTTAAAC GGCAGGAGAA CTGCTTTGGC TTTTACACAT TTAACATGGT ATCTTGGAGG   5160

CTCCTTAGTG CAGTAGAAAG GACATGAACT TCAAGAGTCA GGAGACACAG GGTCTTGCCT   5220

GAGCACTGCC ATCAGATGGC CCCTTACCCT TCTTGAAATG TAATATGCCA GAGGTCGGCC   5280

CAGATATTCT CTGAGCACCC TTCCAGGCCT AAAACACTAG GATACTGTGA GATTAACTCC   5340

TACTTCTGGT CCTTCACTCC TGCCTGTTGG CAGCTCAGTC AGGTAATAGC ACCTGGAGTT   5400

CACCCACCTG GGTGTCCCCC ACTTCTGCTA ATCTCCTCCT CTTGAATCCT TCTTGCTGTT   5460

CAGCTTGGAA ACTAGAATTT AGGAAGAAAA GTCACTGTAT GATGTAATGC ACAGCTTTGG   5520

CCTTGTTTCT GCACAGTAGT GACCCAAACA TCCCCGATAA ACACCCACT GCTTAAGAGG    5580

CAGGCTCGGA TGGACTATAG CTTTGATACC ACAGCCGAAG ACCCTTGGGT TAGGATTTCT   5640

GACTGCATCA AAAACTTATT TAGCCCCATC ATGAGTGAGA ACCATGGCCA CATGCCTCTA   5700
```

```
CAGCCCAATG CCAGCCTGAA TGAAGAAGAA GGGACACAGG GCCACCCAGA TGGGACCCCA    5760

CCAAAGCTGG ACACCGCCAA TGGCACTCCC AAAGTTTACA AGTCAGCAGA CAGCAGCACT    5820

GTGAAGAAAG GTCCTCCTGT GGCTCCCAAG CCAGCCTGGT TTCGCCAAAG CTTGAAAGGT    5880

TTGAGGAATC GTGCTTCAGA CCCAAGAGGG CTCCCTGATC CTGCCTTGTC CACCCAGCCA    5940

GCACCTGCTT CCAGGGAGCA CCTAGGATCA CACATCCGGG CCTCCTCCTC CTCCTCCTCC    6000

ATCAGGCAGA GAATCAGCTC CTTTGAAACC TTTGGCTCCT CTCAACTGCC TGACAAAGGA    6060

GCCCAGAGAC TGAGCCTCCA GCCCTCCTCT GGGGAGGCAG CAAAACCTCT TGGGAAGCAT    6120

GAGGAAGGAC GGTTTTCTGG ACTCTTGGGG CGAGGGGCTG CACCCACTCT TGTGCCCCAG    6180

CAGCCTGAGC AAGTACTGTC CTCGGGGTCC CCTGCAGCCT CCGAGGCCAG AGACCCAGGC    6240

GTGTCTGAGT CCCCTCCCCC AGGGCGGCAG CCCAATCAGA AAACTCTCCC CCCTGGCCCG    6300

GACCCGCTCC TAAGGCTGCT GTCAACACAG GCTGAGGAAT CTCAAGGCCC AGTGCTCAAG    6360

ATGCCTAGCC AGCGAGCACG GAGCTTCCCC CTGACCAGGT CCCAGTCCTG TGAGACGAAG    6420

CTACTTGACG AAAAGACCAG CAAACTCTAT TCTATCAGCA GCCAAGTGTC ATCGGCTGTC    6480

ATGAAATCCT TGCTGTGCCT TCCATCTTCT ATCTCCTGTG CCCAGACTCC CTGCATCCCC    6540

AAGGAAGGGG CATCTCCAAC ATCATCATCC AACGAAGACT CAGCTGCAAA TGGTTCTGCT    6600

GAAACATCTG CCTTGGACAC AGGGTTCTCG CTCAAGTGAG TTTCTACACC CGGTGTTTCT    6660

CTTTACCTTT CTCATCTTTT TCTTTCTCAT CTTTATTTTT AAAAATAATC CTATATATAA    6720

TTTAAAAAAT TCCCAGATAT ATTGATTAAA GAATTGTTCT GCCTCTTTCT TTCCATGTGT    6780

GTGCAGATGT CTGAGTGTGT GTGTGTCTGT CTGTAGGTAT TACACCTCTG CCTTTCACAT    6840

TAAGGAGGAG TTTTCACAAC ATCTGGCTTC AGGAGGGCTG GGAGGTAGGA GGTGGGACTG    6900

GCTCCCTGGT GAATTGCTCA TGAGGGCTGA CATACGCCTG TGGAGATTTG AAGGTTGAT    6960

GCACATCTGA AATGTCCTGC GGTTACTCAG AAAGACCAGA ATGAGGCCAG GAAATTATCC    7020

ATCAGGAATT CTTACTCTCC AAATGGAATC CACTTGTACT CTGCACGTGG GTTCAACTCC    7080

CTCATCAGGG AGTTAGGATG TCTGGGTCCT AGTCTCAGCT TAGGCACTGA TTCTGACTAT    7140

GAGCAGGTTC TTTCCATGCT CACCCTCAGA TTCCTTGTCA GTTGAAATTA GGAGATGGAT    7200

GAGACCTTCT ATGCAGAACC AAGAGGATGT CAGACGTGCC ATAGGGTCCC TGCTGTAGGG    7260

CTGGGGCTTG GTCTTCCCTC TGATCAAAGT AGCTCTGCAT TTATTAGTTT TATTTATTAT    7320

TCTTACACTG CTGGGAAATA TCTGTAGAGT GAAGGTATGC TAGTATCTAC TCATAGATTT    7380

GTTGCATCAA ATAATATGCA CATAAGTGCT TGGCACCACA CCTGGGACAT AGTAATTATA    7440

CAATCACTGT TACCTCTTTT TAATATTGTT GTTCATACTG TGTGTTGTTT CTCCTTATGA    7500

AAGCCTTTCA GAGCTGAGAG AATATACAGA GGGTCTCACG GAAGCCAAGG AAGACGATGA    7560

TGGGGACCAC AGTTCCCTTC AGTCTGGTCA GTCCGTTATC TCCCTGCTGA GCTCAGAAGA    7620

ATTAAAAAAA CTCATCGAGG AGGTGAAGGT TCTGGATGAA GCAACATTAA AGGTAGGTTT    7680

CCTTTGTAAG CATCTGCAGT AACCAATGGC TTATTATGGC TGTGTGGCCA CCTTAGTTGG    7740

GCCAGAGGGG AAGTAGCTTG AGTAGCCTGC CACATCAGAC CCAGGTTGCG TCCTGTGATG    7800

GTGGGACACT GTAGCACTTG ACCACAGTAA GACCTTCCAT TTGAAGAGAG CCTTTTAGCT    7860

TGTGAACCAC TTTCAGTAGA TTGACTTCTT GCATCTTCTT TTGTCATTTT ATAAATGAGA    7920

AAGGTAAGGC TCAATCAAGG CTACAGAACC TGGGTTTTCT GTCTCCAAGT TCAAGTTCAG    7980

TGCTGTTTCC ACATTCCATG TGCTGCTGTC CTGGCATGTG TCTGTTGTGG GATGCTGTCC    8040
```

-continued

```
ATTGTAAACA ATGTGGGTTA CAAGAGCTCT CACCTGGAGC TTTCATTATT TCCACTGTGC    8100
ATGGAGAGGT GGCTGATCCC AGGGCTCACA AGTCCCCCAC GCTTCAGTCA AGTCATTCTG    8160
AAAGTCTCAC TTCCCATATG TTTTCTGAGC ATGACCCAAA GGGGTGTGGG GAGGAAGTGG    8220
CCAGGCTGAG CTGGGGCCAG CAGTCAAATG AGCTCAGGCT CATGGGTCCT GCACCCTCTA    8280
GGTGCTGCCC CAGGCCTCCG TAGGCTTTTG GCACTAGAAT GATCCAGGCT AGGATGAAGA    8340
GGATAAGGAG GTTCTCGTTT TCCATACAAG GAGGCCTCAT AGCTGCAATT TCCACATCAA    8400
GAGTGTAGGT GAGTCTGATG AGCCCAAGGT GCTGCTGTGC TGAGATTCTT TCGGCTGTGG    8460
CTTTCACTTG TCACCTGGGA CCATCATCCC CCAGGATCTT ACTCAGTGCA AATGAAATAA    8520
CAGAGGCAGA GCGTGTAAAA CACAAAGAGC CATCCTGCCT GAGCTGCTCT GGGGAGAGTA    8580
TTTGCTTTCT AACATGAGAA GAGCCTTCTA CAAGGCAAGT AACCTGATAC TTGGGTAAAA    8640
GTTGAGAGAG TTGGGCTAGT GTTGGGGCTT GGAGGTGAGG GTGCAGTGAG GTACATTCAT    8700
CCTTCCATGC CTTTGGGTCT TAGGGCTCC AAGTCTTAGG ATCATAGGGA CAGCTGGAAG    8760
TCAGGTGCTC TAGTGACGCT GAGCAAGTGA ATTCTTTGAC ATAAGTTTAC TCCTTAGTGC    8820
CAAGGTACAA ACAGGTGCCC CAAGAACCTG TAGGTTTACT TTATTTGGTC TGCATGGTGA    8880
TGAAAAAAAT ATTGAATTCT ATACATGATA AAACCTGAAT TGAAACCTGG ACTTTAGGGA    8940
AGTGATCTGG TAGCGCTAGT TCTGTATGCC TACGTAGAGC TGACCCTTTG AGCAGATGTA    9000
CTCGTTGGCG CTCTGCAGTT CCTATCACAC ATCTGCCCAT TTGGCTCATT TTAGGGACCT    9060
GCCTGACTCC TATAGGCATC TGAGTTTGAG ACCCCTGCTC TAGACTGGAA TAGGAGTCTC    9120
TGACTGTGTC CTGGCTCCAT GGGAGTCCCC GTCTAGGCTA GGAAGTACCG TAGTAATGTG    9180
TGTGTGTGTG TGTGTGTGTG TGTGTGTGTC ACACTTGCAC ACTGTGCATT GGGGCAGGAT    9240
GTTAGCTGGG CTTCCTTAGT GCTGCTGCTG TGACCCATGG AGAAGTAGAA GGGAAGAAGG    9300
AGCAACCAAT TCCTGCAGAA CAGCACTGAC CCCTGTTTTG TTTTTTGTTG TTTTTTTTTG    9360
TTTTGTTTTA CCTGAAGTCC TACAACCTGA CTTCATCTCA CACTGTCCAA TATGCTGATT    9420
TCTGGCTGAC TTCATGGCAC TCCCCCTGCC CGGCTGTGGA CAGGGTGAAT GAGAGAGGAA    9480
AATAATTATG CTTGCTGCTT TACATACATT TTTTTTTTCT TCTAAGCTTC CCATGACTCC    9540
TGAAGGTCCA TTCTTTACAG ATGAGGAAAC TGAGGTTTGA GGAGGTGATG TAACTTGGAG    9600
GCTGGCCAAG CTGGGGTTTG AGATAACAAA TCAGTCTGAT GTCAGTCCGA TGTTAAATTG    9660
TTCATCCTCT TGCAGTAAAA TGTTTTTGGA TGTATGTATT TCCTCTGCAG CAATTAGACG    9720
GCATCCATGT CACCATCTTA CACAAGGAGG AAGGTGCTGG TCTTGGGTTC AGCTTGGCAG    9780
GAGGAGCAGA TCTAGAAAAC AAGGTGATTA CGGTGAGTGG CCAAGTGAAG GGCATGTCA    9840
CAGCCAGAGG CAATGGTTCT GGGGAGGGG GACACACTTG CCAGGAAGGG GCCCTGTGCT    9900
GGGGAAATGA AGAATGCATG ACACTAGGCC ACTGGGCAGG TCCTGTCCAC TCAGCACATC    9960
CCAGAGCCTG GGCTGCGTG GAGAGGGTAG CAGGCCTGGC CATGGGCATC TTTTCCTGTG   10020
GGTCCCACTA TTCTGGCTCA TCCAATCTGA TCAGCATTGG CTGCTGCCTT CAGGTCACCT   10080
GTACCTGACC CAGATGGTTT CTGGTTCTGC CAGTTTGTG GAGCCATGCT GCGGCTGCTC   10140
GCTCTCTAAA GCCGAGTGCA TTGCTGTCAT CCCAGGGCTG TGTTGTCTCA GGGTATCCTT   10200
TGTGTAGGCT GTGCTGGGCT CATTTGAATT TCCATGCCCA ACTGAAAACA AATCCTCCAG   10260
TTCACAGCAT CAGCCAGCAT TCAACATACC ACACCCCCTT GCAGTGGCAA TCTGGCATGT   10320
TCCTGCGTGT CACTTCAGAG TCAATCATGT CAGTGGTGAC TTCCTTGATT TCCTGATAAG   10380
TTTTCTATCA CATAAAAAAC ACTTAAAACC GGTAAGTCTC TATTTCTCTC ACTGAGTGCA   10440
```

```
GCTGAGTATT ACAAAAAGAT TCCTGACCGT GTAGTTTACT TTCTACTTGA AGAGGAGGAA   10500

AGAGAGCTTG CCTGTGGGAA TGGCACTTTG GGTATTTTTC TCTGTCCATG AGTAGCAACT   10560

TCTGTCCACG TCATCTGGCC AGTCACCCTT GAGACACTGC AGACAACAGG AAAATAGGAG   10620

GAAGGCGCAC ATGTTGGCTG GGCACATGCA CAAAAGTTCT TTCTCCTTCT GTGTTTGAGC   10680

ATTTCTCTTC CTTTCCAGAT GATTAGAAGG GAACTAACGT AGAGCACCAT CCACGGCCAT   10740

GCTGAGCACT CACTGACCTG TTGTCTAAAT TCATCCTACC CACACTTTGG ATTGATAAAT   10800

TGGTGGCATT TATGCTTCTT TTATAGAGGA GGAACCTGAG GTTCCTCCTT TAATTAACTT   10860

TAATCTTCGT TGGCCTAAAA ATCCTCTAGC ATTGAGGAAC CTGAGGCTCA GAGGAGAGGT   10920

TCCGCTCCAT GCTGGATGTT ACAGCCTGGG GATTCTAACC ATGTAACAGA ATTTTTCTAA   10980

CACCAAAACA ATTTAGAGAA GCAAAGAGCT TTGCTCCTAT CATAAAAGCA AAACTACAGG   11040

TACCACATTT TAGTGGTTTC CATGCATGCT ATCACTCAGT CCTCTTAATT ATAATGGACC   11100

TCATTAAAGA GGCTGAGGCA GAGACATGAG ATATTTTTGT GTGTTTGTTT ATCCCACATA   11160

TCTTGCAGAA AGGGGACCAA GAGGTGACTG GAGGTAAAGA GTCAGAATTT CTAGGGGAGG   11220

AGCTATAAAA ATGTCTAGAC TGCCTAGGAG AGTGTTTCTC AAAATGCATT CTGCCAAATG   11280

AGACCGAGAA TTTCTCTATG AGAAAAGAAT TCTTTGTTGA AACACTTTGG GAATCCCCAT   11340

AATACCCTGC CAACTTAGAA ATCTGCCATG CAGATTTGCA TTGTAGACCC TCTAAATGCC   11400

TTTTGCTTAG AAATCTGCTG CCATGCAAAT TTGCATTGTA GACCCTCTAA TGCCTTTTGC   11460

TTTTTAAAAG TAGACAATGT CAGAGCTTTT GTTTCACCCA GTATTCCTCA AGTTTCTTTG   11520

ATTTTAAAAA ATTTTTCTTG GCCGGGTGTG GTGGCTCATA CCTGTAATTC CAACACTGTG   11580

CGGGGCCAAG GTGAGAGGAT TGCTTGAGCC CAGGAGTTTG AGACCATCCT GGGCAACACT   11640

GGGAGACCTG TCTCTATTTT TTAAAAAATA ATAGGAAAAG CCTTTTTCTT ACACAATACC   11700

CGTTAATATG CCATAGAATC AGTGCCTTGA GAAAACTACT CTGGGGACTT CTGACCTAGG   11760

GCAGGTGAAG CAAAAGATTT TATATGGAAT CCCAACTAGA ATCGTGGTGG TACACTATAG   11820

GACGTTGTGT TGGGATGGAT TCTGAGGGCT TACCTGGTCA TTACTGCTGG TGATCTCTGC   11880

TCTGGATGGA GAAGGAGGGA ATGCTGGCCT CTGTGCCAGC AGCTCCAATC TAGGACACAA   11940

TTATCTTTAA TCTTTGTTGG CCTAAAAATC CTCTAGCATT GACTAACCGG TTCAATCCTC   12000

CTCCAGCAAG TATGTGGACT GGACTTGTGT GATTTCTGGT CCTGACTTCC TTTGGTTTGC   12060

TCAGGTTCAC AGAGTGTTTC CAAATGGGCT GGCCTCCCAG GAAGGGACTA TTCAGAAGGG   12120

CAATGAGGTT CTTTCCATCA ACGGCAAGTC TCTCAAGGGG ACCACGCACC ATGATGCCTT   12180

GGCAATCCTC CGCCAAGCTC GAGAGCCCAG GCAAGCTGTG ATTGTCACAA GGAAGCTGAC   12240

TCCAGAGGCC ATGCCCGACC TCAACTCCTC CACTGACTCT GCAGCCTCAG CCTCTGCAGC   12300

CAGTGATGTT TCTGTAGAAT CTAGTAAGTT CTCCCAACTC AGTGGAAGCC ACATGGGCCA   12360

CATCCTCTTT GGCCATTTGG GGCCAGACCT GATGGGCTA CTCAGTAATT TGTGACCCCA   12420

AGAATGTGTG GCTGCCTAGT ACACTGCCTG AGACGTGTTT ACATGTGCCT GTGTGCAAAC   12480

ACGGGGCTG TATCACCCCG GGCTCACTTG AAGCCCAGGG CATCTGTGGC CTGGGGAGAG   12540

GAGAGGATCC CTAACAGAGA CCTTGTGTTT TTCTCAGCAG CAGAGGCCAC AGTCTGCACG   12600

GTGACACTGG AGAAGATGTC GGCAGGGCTG GGCTTCAGCC TGGAAGGAGG GAAGGGCTCC   12660

CTACACGGAG ACAAGCCTCT CACCATTAAC AGGATTTTCA AAGGTGTGGG GTGTGTCTGG   12720

TTCTTTGCGT GCTCTCCAGT TGTGGGCATG TGGCCAGGCC CCCAAAAGGC TTCTGGGCAC   12780
```

```
TTTCTGGGCT ATGTTGTTTC CCACAACTCC ATGTCCTCTT CATAGGCATG CTGGTCCTTT    12840

TAGGGCTCAA TTCTGCTTTT TCTACTTTTT CTCCTTTGCT CAGACATCCC CTCAATCCCC    12900

CCTCTGTTTT GATGGGTCTT CAAAAATACC TAAGTCCTGG GCTTGGTTCG GGTTGGCAGG    12960

GCCAGGACTC TAGAGTGGGG CAGTGAGGCA CTGGCCTGTG GGGCAGAATT TTAAAGGGGT    13020

GCCAAAACAC TCAGTAACTC AGATCGATAC TATTTTAATG CAGCGTGTTT TTTAAAATTA    13080

ATTTTAAAAA AACATGTTGG GACAAAATAT CCAAGTTTTA AATCAAGACA GAGTCTGACT    13140

TTGTACTGCA CACTTGGCCT CATTTGCCTT ACCCTAGTCC TGGACACGTC AGCTCCTGCC    13200

TTTATTTAAA ATGTTGATAG ATATTTTGTT CATCAGGGAT TGGAGTACAA ACCAGTCTGA    13260

TATGGGGTC ACTTGGATTT CCCTGTGAAA ATCATGAATG ACTGTGGCTA CCATGTAAAA    13320

CCATCCCTGA TTCTTTGGTG TTCCTCAAAT TGGAGGTCTC CAAGCCACAG AGCAAGGGGT    13380

TGTAGAGAGA GGAGTACTGG ACAGGGAGGC AGGTGGGCCA GGTTCTAGTC CCAGCTCTGC    13440

CTGTAATGTG CTGAGTGACC CTTCCCTTCT GGGCCTGAGG CTCTTCATCC ATAAAAGGAG    13500

GTAAAGAGGT ACAGGTGTGT GTCTGAGGGC TCTTAGGACT GAGACCCAAA GGGACTCTTA    13560

GCTCTGTCCC TCACCCACTA TGAGCTCCTG CTGCTGACTG GTTTCGTTAG AGGAAGTTCT    13620

GGCTGCGGCT GCAGAAACCC AGAAGGTAGA GTGAGGCTTA CATGGCATTC CCCCCAGAAT    13680

CCATGTTAAC CCCAATTCTG GGAAAGATAT TTCTAATTTT TGAAGGTCAA TTTGGAAGGA    13740

GCATTGGGTT CAATGTCAAG AGGACTAGAT TCCAGTGTTA GTTCTGCCAC ATGACCTTGG    13800

TAGCATGATC TTGGACAAGT CACTTCACCA CCATGGGCCC ATTTGCTTAA ATGTTTAGGA    13860

TGAGACTGCC AGCTGCAGGG TGATGTTGGA AGGAGAGATG CAGATTCTGG AGCCAGAAAG    13920

TCTGGGTTCC AGCCCAGGGC CCACCACTAG CAGCTATGAA GCTCTGGGCC AGTTACTTGA    13980

GTTCTTGGTT TCCTCAGCTG TTAAAAGGAA ACACAAATAA TACACCCCTC ATAGGATTAC    14040

TGTCATAAAT GCAAAACATT AGCACAACGC CTGTTAAAAT AATTGCCCAA TACACTTTAG    14100

CTATATTTTC ATTACTATCA TTAGTATTAT CTTCTACTCT TATCAGGATT TGTGAAGATC    14160

AACTGTGTCA AATGGATGGG AAATTTTATT TTAAATAAAA CAGTAAAATA GCATTGTTTT    14220

CACTTGCAGC TTTGAAATAG TGGGGCCAT ATATGGTTGT TTCCTTTTTT ATGTGGACAC    14280

AGAGGACTTC GTGCCAGAGG CAAGATCCCT GTAAATATTG TTGCACAAAA ATCTCACTAG    14340

CTCTCTTCCC ATACCACCCA ATGCTGATGT CCTCACCACA TGCGGAGAAC AAATGTGAAG    14400

GGAGTAGGAT ATTGGGTCAG TGTCCAAAGC AGGGTCTGGG CAGGACTCAG CTCCCCAGAG    14460

TCCTCTATGA ACTATGGACG GTGCTCCAGG CAGGCTAAGG CGTGGAGCTG CCTGATATTT    14520

CCCTCCCCTG GGGACAGCAA GGGCTATCCC TTTCCAAAGG CCATGGAGAG CTGGAGCCTG    14580

GTGCCCTAAC TTTTGAGTCA CCATCTTAAG AGATGCCTCA TTTTAGAACC ACCAACAAGC    14640

AAGCTCCCAA GGGATGGTGC CCTGTTCTCT ACCAAGCTAT CCTGGCTCTT TGGAGATCAA    14700

GGAGAGGAGG CAACTTTCCT TGTTCCCCAT CATCTGTGGA ACCCATTACC TTCTCCCTCA    14760

TTTCAGGAGC AGCCTCAGAA CAAAGTGAGA CAGTCCAGCC TGGAGATGAA ATCTTGCAGC    14820

TGGGTGGCAC TGCCATGCAG GGCCTCACAC GGTTTGAAGC CTGGAACATC ATCAAGGCAC    14880

TGCCTGATGG ACCTGTCACG ATTGTCATCA GGAGAAAAAG CCTCCAGTCC AAGGAAACCA    14940

CAGCTGCTGG AGACTCCTAG GCAGGACATG CTGAAGCCAA AGCCAATAAC ACACAGCTAA    15000

CACACAGCTC CCATAACCGC TGATTCTCAG GGTCTCTGCT GCCGCCCCAC CCAGATGGGG    15060

GAAAGCACAG GTGGGCTTCC CAGTGGCTGC TGCCCAGGCC CAGACCTTCT AGGACGCCAC    15120

CCAGCAAAAG GTTGTTCCTA AAATAAGGGC AGAGTCACAC GGGGGCAGCT GATACAAATT    15180
```

```
GCAGACTGTG TAAAAAGAGA GCTTAATGAT AATATTGTGG TGCCACAAAT AAAATGGATT    15240

TATTAGAATT TCATATGACA TTCATGCCTG GCTTCGCAAA ATGTTTCAAG TACTGTAACT    15300

GTGTCATGAT TCACCCCCAA ACAGTGACAT TTATTTTTCT CATGAATCTG CAATGTGGGC    15360

AGAGATTGGA ATGGGCAGCT CATCTCTGTC CCACTTGGCA TCAGCTGGCG TCATGCAAAG    15420

TCATGCAAAG GCTGGGACCA CGTGAGATCA TTCACTCATA CATCTGGCCG TTGATGTTGG    15480

CTGGGAACTC ACCTGGGGCT GCTGGCCTGA ATGCTTATAG GTGGCCTCTC CTTGTGGCCT    15540

GGCCTCCTCA CAACATGGTG TCTGGATTCC CAGGATGAGC ATCCCAGGAT CGCAAGAGCC    15600

ACGTAGAAGC TGCATCTTGT TTATACCTTT GCCTTGGAAG TTGCATGGCA TCACCTCCAC    15660

CATACTCCAT CAGTTAGAGC TGACACAAAC CTGCCTGGGT TTAAGGGGAG AGGAAATATT    15720

GCTGGGGTCA TTTATGAAAA ATACAGTTTG TCACATGAAA CATTTGCAAA ATTGTTTTTG    15780

GTTGGATTGG AGAAGTAATC CTAGGGAAGG GTGGTGGAGC CAGTAAACAG AGGAGTACAG    15840

GTGAAGCACC AAGCTCAAAG CGTGGACAGG TGTGCCGACA GAAGGAACCA GCGTGTATAT    15900

GAGGGTATCA AATAAAATTG CTACTACTTA CCTACC                              15936
```

(2) INFORMATION FOR SEQ ID NO: 2:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: other nucleic acid
        (A) DESCRIPTION:   /desc = "Primer"

(xi) SEQUENCE DESCRIPTION: SEQ ID NO: 2:

```
CTTTTCGTCA AGTAGCTTCG TCTCACAG                                          28
```

(2) INFORMATION FOR SEQ ID NO: 3:

(i) SEQUENCE CHARACTERISTICS:
        (A) LENGTH: 47 base pairs
        (B) TYPE: nucleic acid
        (C) STRANDEDNESS: single
        (D) TOPOLOGY: linear (ii) MOLECULE TYPE: other nucleic acid
        (A) DESCRIPTION:   /desc = "Primer"

(xi) SEQUENCE DESCRIPTION: SEQ ID NO: 3:

```
GAAATCGAAG CGGCCGCGCT CCGTGCTCGC TGGCTAGGCA TCTTGAG                     47
```

(2) INFORMATION FOR SEQ ID NO: 4:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid
        (A) DESCRIPTION:   /desc = "Primer"

(xi) SEQUENCE DESCRIPTION: SEQ ID NO: 4:

```
GGTCGACGGC CCGGGCTGGT                                                   20
```

(2) INFORMATION FOR SEQ ID NO: 5:

(i) SEQUENCE CHARACTERISTICS:

(A) LENGTH: 9096 base pairs
        (B) TYPE: nucleic acid
        (C) STRANDEDNESS: double
        (D) TOPOLOGY: linear (ii) MOLECULE TYPE: DNA (ix) FEATURE:
        (A) NAME/KEY: exon
        (B) LOCATION:1..338

(ix) FEATURE:
        (A) NAME/KEY: intron
        (B) LOCATION:339..663

(ix) FEATURE:
        (A) NAME/KEY: exon
        (B) LOCATION:664..832

(ix) FEATURE:
        (A) NAME/KEY: intron
        (B) LOCATION:833..2870

(ix) FEATURE:
        (A) NAME/KEY: exon
        (B) LOCATION:2871..2972

(ix) FEATURE:
        (A) NAME/KEY: intron
        (B) LOCATION:2973..5224

(ix) FEATURE:
        (A) NAME/KEY: exon
        (B) LOCATION:5225..5483

(ix) FEATURE:
        (A) NAME/KEY: intron
        (B) LOCATION:5484..5737

(ix) FEATURE:
        (A) NAME/KEY: exon
        (B) LOCATION:5738..5863

(ix) FEATURE:
        (A) NAME/KEY: intron
        (B) LOCATION:5864..7926

(ix) FEATURE:
        (A) NAME/KEY: exon
        (B) LOCATION:7927..9096

(ix) FEATURE:
        (A) NAME/KEY: -
        (B) LOCATION:356
        (D) OTHER INFORMATION:/product= "N means between 1 -
            about 6 bp"

(xi) SEQUENCE DESCRIPTION: SEQ ID NO: 5:

```
CCGGACCCGC TCCTAAGGCT GCTGTCAACA CAGGCTGAGG AATCTCAAGG CCCAGTGCTC      60

AAGATGCCTA GCCAGCGAGC ACGGAGCTTC CCCCTGACCA GGTCCCAGTC CTGTGAGACG     120

AAGCTACTTG ACGAAAAGAC CAGCAAACTC TATTCTATCA GCAGCCAAGT GTCATCGGCT     180

GTCATGAAAT CCTTGCTGTG CCTTCCATCT TCTATCTCCT GTGCCCAGAC TCCCTGCATC     240

CCCAAGGAAG GGGCATCTCC AACATCATCA TCCAACGAAG ACTCAGCTGC AAATGGTTCT     300

GCTGAAACAT CTGCCTTGGA CACAGGGTTC TCGCTCAAGT GAGTTTCTAC ACCCGNGGAT     360

GAGACCTTCT ATGCAGAACC AAGAGGATGT CAGACGTGCC ATAGGGTCCC TGCTGTAGGG     420

CTGGGGCTTG GTCTTCCCTC TGATCAAAGT AGCTCTGCAT TTATTAGTTT TATTTATTAT     480

TCTTACACTG CTGGGAAATA TCTGTAGAGT GAAGGTATGC TAGTATCTAC TCATAGATTT     540

GTTGCATCAA ATAATATGCA CATAAGTGCT TGGCACCACA CCTGGGACAT AGTAATTATA     600
```

```
CAATCACTGT TACCTCTTTT TAATATTGTT GTTCATACTG TGTGTTGTTT CTCCTTATGA      660

AAGCCTTTCA GAGCTGAGAG AATATACAGA GGGTCTCACG GAAGCCAAGG AAGACGATGA      720

TGGGACCAC AGTTCCCTTC AGTCTGGTCA GTCCGTTATC TCCCTGCTGA GCTCAGAAGA       780

ATTAAAAAAA CTCATCGAGG AGGTGAAGGT TCTGGATGAA GCAACATTAA AGGTAGGTTT     840

CCTTTGTAAG CATCTGCAGT AACCAATGGC TTATTATGGC TGTGTGGCCA CCTTAGTTGG     900

GCCAGAGGGG AAGTAGCTTG AGTAGCCTGC CACATCAGAC CCAGGTTGCG TCCTGTGATG     960

GTGGGACACT GTAGCACTTG ACCACAGTAA GACCTTCCAT TTGAAGAGAG CCTTTTAGCT    1020

TGTGAACCAC TTTCAGTAGA TTGACTTCTT GCATCTTCTT TTGTCATTTT ATAAATGAGA    1080

AAGGTAAGGC TCAATCAAGG CTACAGAACC TGGGTTTTCT GTCTCCAAGT TCAAGTTCAG    1140

TGCTGTTTCC ACATTCCATG TGCTGCTGTC CTGGCATGTG TCTGTTGTGG GATGCTGTCC    1200

ATTGTAAACA ATGTGGGTTA CAAGAGCTCT CACCTGGAGC TTTCATTATT CCACTGTGC     1260

ATGGAGAGGT GGCTGATCCC AGGGCTCACA AGTCCCCAC GCTTCAGTCA AGTCATTCTG     1320

AAAGTCTCAC TTCCCATATG TTTTCTGAGC ATGACCCAAA GGGGTGTGGG GAGGAAGTGG    1380

CCAGGCTGAG CTGGGGCCAG CAGTCAAATG AGCTCAGGCT CATGGGTCCT GCACCCTCTA    1440

GGTGCTGCCC CAGGCCTCCG TAGGCTTTTG GCACTAGAAT GATCCAGGCT AGGATGAAGA    1500

GGATAAGGAG GTTCTCGTTT TCCATACAAG GAGGCCTCAT AGCTGCAATT TCCACATCAA    1560

GAGTGTAGGT GAGTCTGATG AGCCCAAGGT GCTGCTGTGC TGAGATTCTT TCGGCTGTGG    1620

CTTTCACTTG TCACCTGGGA CCATCATCCC CCAGGATCTT ACTCAGTGCA AATGAAATAA    1680

CAGAGGCAGA GCGTGTAAAA CACAAAGAGC CATCCTGCCT GAGCTGCTCT GGGGAGAGTA    1740

TTTGCTTTCT AACATGAGAA GAGCCTTCTA CAAGGCAAGT AACCTGATAC TTGGGTAAAA    1800

GTTGAGAGAG TTGGGCTAGT GTTGGGGCTT GGAGGTGAGG GTGCAGTGAG GTACATTCAT    1860

CCTTCCATGC CTTTGGGTCT TAGGGCTCC AAGTCTTAGG ATCATAGGGA CAGCTGGAAG     1920

TCAGGTGCTC TAGTGACGCT GAGCAAGTGA ATTCTTTGAC ATAAGTTTAC TCCTTAGTGC    1980

CAAGGTACAA ACAGGTGCCC CAAGAACCTG TAGGTTTACT TTATTTGGTC TGCATGGTGA    2040

TGAAAAAAAT ATTGAATTCT ATACATGATA AAACCTGAAT TGAAACCTGG ACTTTAGGGA    2100

AGTGATCTGG TAGCGCTAGT TCTGTATGCC TACGTAGAGC TGACCCTTTG AGCAGATGTA    2160

CTCGTTGGCG CTCTGCAGTT CCTATCACAC ATCTGCCCAT TTGGCTCATT TTAGGGACCT    2220

GCCTGACTCC TATAGGCATC TGAGTTTGAG ACCCCTGCTC TAGACTGGAA TAGGAGTCTC    2280

TGACTGTGTC CTGGCTCCAT GGGAGTCCCC GTCTAGGCTA GGAAGTACCG TAGTAATGTG    2340

TGTGTGTGTG TGTGTGTGTG TGTGTGTGTC ACACTTGCAC ACTGTGCATT GGGGCAGGAT    2400

GTTAGCTGGG CTTCCTTAGT GCTGCTGCTG TGACCCATGG AGAAGTAGAA GGGAAGAAGG    2460

AGCAACCAAT TCCTGCAGAA CAGCACTGAC CCCTGTTTTG TTTTTTGTTG TTTTTTTTTG    2520

TTTTGTTTTA CCTGAAGTCC TACAACCTGA CTTCATCTCA CACTGTCCAA TATGCTGATT    2580

TCTGGCTGAC TTCATGGCAC TCCCCCTGCC CGGCTGTGGA CAGGGTGAAT GAGAGAGGAA    2640

AATAATTATG CTTGCTGCTT TACATACATT TTTTTTTTCT TCTAAGCTTC CCATGACTCC    2700

TGAAGGTCCA TTCTTTACAG ATGAGGAAAC TGAGGTTTGA GGAGGTGATG TAACTTGGAG    2760

GCTGGCCAAG CTGGGGTTTG AGATAACAAA TCAGTCTGAT GTCAGTCCGA TGTTAAATTG    2820

TTCATCCTCT TGCAGTAAAA TGTTTTTGGA TGTATGTATT TCCTCTGCAG CAATTAGACG    2880

GCATCCATGT CACCATCTTA CACAAGGAGG AAGGTGCTGG TCTTGGGTTC AGCTTGGCAG    2940

GAGGAGCAGA TCTAGAAAAC AAGGTGATTA CGGTGAGTGG CCAAGTGAAG GGGCATGTCA    3000
```

```
CAGCCAGAGG CAATGGTTCT GGGGGAGGGG GACACACTTG CCAGGAAGGG GCCCTGTGCT   3060

GGGGAAATGA AGAATGCATG ACACTAGGCC ACTGGGCAGG TCCTGTCCAC TCAGCACATC   3120

CCAGAGCCTG GGGCTGCGTG GAGAGGGTAG CAGGCCTGGC CATGGGCATC TTTTCCTGTG   3180

GGTCCCACTA TTCTGGCTCA TCCAATCTGA TCAGCATTGG CTGCTGCCTT CAGGTCACCT   3240

GTACCTGACC CAGATGGTTT CTGGTTCTGC CAGTTTTGTG GAGCCATGCT GCGGCTGCTC   3300

GCTCTCTAAA GCCGAGTGCA TTGCTGTCAT CCCAGGGCTG TGTTGTCTCA GGGTATCCTT   3360

TGTGTAGGCT GTGCTGGGCT CATTTGAATT TCCATGCCCA ACTGAAAACA AATCCTCCAG   3420

TTCACAGCAT CAGCCAGCAT TCAACATACC ACACCCCCTT GCAGTGGCAA TCTGGCATGT   3480

TCCTGCGTGT CACTTCAGAG TCAATCATGT CAGTGGTGAC TTCCTTGATT TCCTGATAAG   3540

TTTTCTATCA CATAAAAAAC ACTTAAAACC GGTAAGTCTC TATTTCTCTC ACTGAGTGCA   3600

GCTGAGTATT ACAAAAAGAT TCCTGACCGT GTAGTTTACT TTCTACTTGA AGAGGAGGAA   3660

AGAGAGCTTG CCTGTGGGAA TGGCACTTTG GGTATTTTTC TCTGTCCATG AGTAGCAACT   3720

TCTGTCCACG TCATCTGGCC AGTCACCCTT GAGACACTGC AGACAACAGG AAAATAGGAG   3780

GAAGGCGCAC ATGTTGGCTG GCACATGCA CAAAAGTTCT TTCTCCTTCT GTGTTTGAGC   3840

ATTTCTCTTC CTTTCCAGAT GATTAGAAGG GAACTAACGT AGAGCACCAT CCACGGCCAT   3900

GCTGAGCACT CACTGACCTG TTGTCTAAAT TCATCCTACC CACACTTTGG ATTGATAAAT   3960

TGGTGGCATT TATGCTTCTT TTATAGAGGA GGAACCTGAG GTTCCTCCTT TAATTAACTT   4020

TAATCTTCGT TGGCCTAAAA ATCCTCTAGC ATTGAGGAAC CTGAGGCTCA GAGGAGAGGT   4080

TCCGCTCCAT GCTGGATGTT ACAGCCTGGG GATTCTAACC ATGTAACAGA ATTTTTCTAA   4140

CACCAAAACA ATTTAGAGAA GCAAAGAGCT TTGCTCCTAT CATAAAAGCA AAACTACAGG   4200

TACCACATTT TAGTGGTTTC CATGCATGCT ATCACTCAGT CCTCTTAATT ATAATGGACC   4260

TCATTAAAGA GGCTGAGGCA GAGACATGAG ATATTTTTGT GTGTTTGTTT ATCCCACATA   4320

TCTTGCAGAA AGGGGACCAA GAGGTGACTG GAGGTAAAGA GTCAGAATTT CTAGGGGAGG   4380

AGCTATAAAA ATGTCTAGAC TGCCTAGGAG AGTGTTTCTC AAAATGCATT CTGCCAAATG   4440

AGACCGAGAA TTTCTCTATG AGAAAAGAAT TCTTTGTTGA AACACTTTGG GAATCCCCAT   4500

AATACCCTGC CAACTTAGAA ATCTGCCATG CAGATTTGCA TTGTAGACCC TCTAAATGCC   4560

TTTTGCTTAG AAATCTGCTG CCATGCAAAT TTGCATTGTA GACCCTCTAA TGCCTTTTGC   4620

TTTTTAAAAG TAGACAATGT CAGAGCTTTT GTTTCACCCA GTATTCCTCA AGTTTCTTTG   4680

ATTTTAAAAA ATTTTTCTTG GCCGGGTGTG GTGGCTCATA CCTGTAATTC CAACACTGTG   4740

CGGGGCCAAG GTGAGAGGAT TGCTTGAGCC CAGGAGTTTG AGACCATCCT GGGCAACACT   4800

GGGAGACCTG TCTCTATTTT TTAAAAAATA ATAGGAAAAG CCTTTTTCTT ACACAATACC   4860

CGTTAATATG CCATAGAATC AGTGCCTTGA GAAAACTACT CTGGGGACTT CTGACCTAGG   4920

GCAGGTGAAG CAAAAGATTT TATATGGAAT CCCAACTAGA ATCGTGGTGG TACACTATAG   4980

GACGTTGTGT TGGGATGGAT TCTGAGGGCT TACCTGGTCA TTACTGCTGG TGATCTCTGC   5040

TCTGGATGGA GAAGGAGGGA ATGCTGGCCT CTGTGCCAGC AGCTCCAATC TAGGACACAA   5100

TTATCTTTAA TCTTTGTTGG CCTAAAAATC CTCTAGCATT GACTAACCGG TTCAATCCTC   5160

CTCCAGCAAG TATGTGGACT GGACTTGTGT GATTTCTGGT CCTGACTTCC TTTGGTTTGC   5220

TCAGGTTCAC AGAGTGTTTC CAAATGGGCT GGCCTCCCAG GAAGGGACTA TTCAGAAGGG   5280

CAATGAGGTT CTTTCCATCA ACGGCAAGTC TCTCAAGGGG ACCACGCACC ATGATGCCTT   5340
```

-continued

```
GGCAATCCTC CGCCAAGCTC GAGAGCCCAG GCAAGCTGTG ATTGTCACAA GGAAGCTGAC     5400

TCCAGAGGCC ATGCCCGACC TCAACTCCTC CACTGACTCT GCAGCCTCAG CCTCTGCAGC     5460

CAGTGATGTT TCTGTAGAAT CTAGTAAGTT CTCCCAACTC AGTGGAAGCC ACATGGGCCA     5520

CATCCTCTTT GGCCATTTGG GGCCAGACCT GATGGGCTA CTCAGTAATT TGTGACCCCA      5580

AGAATGTGTG GCTGCCTAGT ACACTGCCTG AGACGTGTTT ACATGTGCCT GTGTGCAAAC     5640

ACGGGGCTG TATCACCCCG GGCTCACTTG AAGCCCAGGG CATCTGTGGC CTGGGGAGAG      5700

GAGAGGATCC CTAACAGAGA CCTTGTGTTT TTCTCAGCAG CAGAGGCCAC AGTCTGCACG     5760

GTGACACTGG AGAAGATGTC GGCAGGGCTG GGCTTCAGCC TGGAAGGAGG GAAGGGCTCC     5820

CTACACGGAG ACAAGCCTCT CACCATTAAC AGGATTTTCA AAGGTGTGGG GTGTGTCTGG     5880

TTCTTTGCGT GCTCTCCAGT TGTGGGCATG TGGCCAGGCC CCCAAAAGGC TTCTGGGCAC     5940

TTTCTGGGCT ATGTTGTTTC CCACAACTCC ATGTCCTCTT CATAGGCATG CTGGTCCTTT     6000

TAGGGCTCAA TTCTGCTTTT TCTACTTTTT CTCCTTTGCT CAGACATCCC CTCAATCCCC     6060

CCTCTGTTTT GATGGGTCTT CAAAAATACC TAAGTCCTGG GCTTGGTTCG GGTTGGCAGG     6120

GCCAGGACTC TAGAGTGGGG CAGTGAGGCA CTGGCCTGTG GGGCAGAATT TTAAAGGGGT     6180

GCCAAAACAC TCAGTAACTC AGATCGATAC TATTTTAATG CAGCGTGTTT TTTAAAATTA     6240

ATTTTAAAAA AACATGTTGG GACAAAATAT CCAAGTTTTA AATCAAGACA GAGTCTGACT     6300

TTGTACTGCA CACTTGGCCT CATTTGCCTT ACCCTAGTCC TGGACACGTC AGCTCCTGCC     6360

TTTATTTAAA ATGTTGATAG ATATTTTGTT CATCAGGGAT TGGAGTACAA ACCAGTCTGA     6420

TATGGGGGTC ACTTGGATTT CCCTGTGAAA ATCATGAATG ACTGTGGCTA CCATGTAAAA     6480

CCATCCCTGA TTCTTTGGTG TTCCTCAAAT TGGAGGTCTC CAAGCCACAG AGCAAGGGGT     6540

TGTAGAGAGA GGAGTACTGG ACAGGGAGGC AGGTGGGCCA GGTTCTAGTC CCAGCTCTGC     6600

CTGTAATGTG CTGAGTGACC CTTCCCTTCT GGGCCTGAGG CTCTTCATCC ATAAAAGGAG     6660

GTAAAGAGGT ACAGGTGTGT GTCTGAGGGC TCTTAGGACT GAGACCCAAA GGGACTCTTA     6720

GCTCTGTCCC TCACCCACTA TGAGCTCCTG CTGCTGACTG GTTTCGTTAG AGGAAGTTCT     6780

GGCTGCGGCT GCAGAAACCC AGAAGGTAGA GTGAGGCTTA CATGGCATTC CCCCCAGAAT     6840

CCATGTTAAC CCCAATTCTG GGAAAGATAT TTCTAATTTT TGAAGGTCAA TTTGAAGGA      6900

GCATTGGGTT CAATGTCAAG AGGACTAGAT TCCAGTGTTA GTTCTGCCAC ATGACCTTGG     6960

TAGCATGATC TTGGACAAGT CACTTCCACC CCATGGGCCC ATTTGCTTAA ATGTTTAGGA     7020

TGAGACTGCC AGCTGCAGGG TGATGTTGGA AGGAGAGATG CAGATTCTGG AGCCAGAAAG     7080

TCTGGGTTCC AGCCCAGGGC CCACCACTAG CAGCTATGAA GCTCTGGGCC AGTTACTTGA     7140

GTTCTTGGTT TCCTCAGCTG TTAAAAGGAA ACACAAATAA TACACCCCTC ATAGGATTAC     7200

TGTCATAAAT GCAAAACATT AGCACAACGC CTGTTAAAAT AATTGCCCAA TACACTTTAG     7260

CTATATTTTC ATTACTATCA TTAGTATTAT CTTCTACTCT TATCAGGATT TGTGAAGATC     7320

AACTGTGTCA AATGGATGGG AAATTTTATT TTAATATAAA CAGTAAAATA GCATTGTTTT     7380

CACTTGCAGC TTTGAAATAG TGGGGGCCAT ATATGGTTGT TTCCTTTTTT ATGTGGACAC     7440

AGAGGACTTC GTGCCAGAGG CAAGATCCCT GTAAATATTG TTGCACAAAA ATCTCACTAG     7500

CTCTCTTCCC ATACCACCCA ATGCTGATGT CCTCACCACA TGCGGAGAAC AAATGTGAAG     7560

GGAGTAGGAT ATTGGGTCAG TGTCCAAAGC AGGGTCTGGG CAGGACTCAG CTCCCCAGAG     7620

TCCTCTATGA ACTATGGACG GTGCTCCAGG CAGGCTAAGG CGTGGAGCTG CCTGATATTT     7680

CCCTCCCCTG GGGACAGCAA GGGCTATCCC TTTCCAAAGG CCATGGAGAG CTGGAGCCTG     7740
```

```
GTGCCCTAAC TTTTGAGTCA CCATCTTAAG AGATGCCTCA TTTTAGAACC ACCAACAAGC      7800

AAGCTCCCAA GGGATGGTGC CCTGTTCTCT ACCAAGCTAT CCTGGCTCTT TGGAGATCAA      7860

GGAGAGGAGG CAACTTTCCT TGTTCCCCAT CATCTGTGGA ACCCATTACC TTCTCCCTCA      7920

TTTCAGGAGC AGCCTCAGAA CAAAGTGAGA CAGTCCAGCC TGGAGATGAA ATCTTGCAGC      7980

TGGGTGGCAC TGCCATGCAG GGCCTCACAC GGTTTGAAGC CTGGAACATC ATCAAGGCAC      8040

TGCCTGATGG ACCTGTCACG ATTGTCATCA GGAGAAAAAG CCTCCAGTCC AAGGAAACCA      8100

CAGCTGCTGG AGACTCCTAG GCAGGACATG CTGAAGCCAA AGCCAATAAC ACACAGCTAA      8160

CACACAGCTC CCATAACCGC TGATTCTCAG GGTCTCTGCT GCCGCCCCAC CCAGATGGGG      8220

GAAAGCACAG GTGGGCTTCC CAGTGGCTGC TGCCCAGGCC CAGACCTTCT AGGACGCCAC      8280

CCAGCAAAAG GTTGTTCCTA AAATAAGGGC AGAGTCACAC GGGGGCAGCT GATACAAATT      8340

GCAGACTGTG TAAAAAGAGA GCTTAATGAT AATATTGTGG TGCCACAAAT AAAATGGATT      8400

TATTAGAATT TCATATGACA TTCATGCCTG GCTTCGCAAA ATGTTTCAAG TACTGTAACT      8460

GTGTCATGAT TCACCCCCAA ACAGTGACAT TTATTTTTCT CATGAATCTG CAATGTGGGC      8520

AGAGATTGGA ATGGGCAGCT CATCTCTGTC CCACTTGGCA TCAGCTGGCG TCATGCAAAG      8580

TCATGCAAAG GCTGGGACCA CGTGAGATCA TTCACTCATA CATCTGGCCG TTGATGTTGG      8640

CTGGGAACTC ACCTGGGGCT GCTGGCCTGA ATGCTTATAG GTGGCCTCTC CTTGTGGCCT      8700

GGCCTCCTCA CAACATGGTG TCTGGATTCC CAGGATGAGC ATCCCAGGAT CGCAAGAGCC      8760

ACGTAGAAGC TGCATCTTGT TTATACCTTT GCCTTGGAAG TTGCATGGCA TCACCTCCAC      8820

CATACTCCAT CAGTTAGAGC TGACACAAAC CTGCCTGGGT TTAAGGGGAG AGGAAATATT      8880

GCTGGGGTCA TTTATGAAAA ATACAGTTTG TCACATGAAA CATTTGCAAA ATTGTTTTTG      8940

GTTGGATTGG AGAAGTAATC CTAGGGAAGG GTGGTGGAGC CAGTAAACAG AGGAGTACAG      9000

GTGAAGCACC AAGCTCAAAG CGTGGACAGG TGTGCCGACA GAAGGAACCA GCGTGTATAT      9060

GAGGGTATCA AATAAAATTG CTACTACTTA CCTACC                               9096
```

(2) INFORMATION FOR SEQ ID NO: 6:

(i) SEQUENCE CHARACTERISTICS:
        (A) LENGTH: 3061 base pairs
        (B) TYPE: nucleic acid
        (C) STRANDEDNESS: double
        (D) TOPOLOGY: linear (ii) MOLECULE TYPE: cDNA (ix) FEATURE:
        (A) NAME/KEY: CDS
        (B) LOCATION:190..2085

(ix) FEATURE:
        (A) NAME/KEY: 3'UTR
        (B) LOCATION:2086..3061

(ix) FEATURE:
        (A) NAME/KEY: 5'UTR
        (B) LOCATION:1..189

(xi) SEQUENCE DESCRIPTION: SEQ ID NO: 6:

```
CTGCTGCCAC TGCTGCTACC ACAGGAAGAC ACAGCAGGGA GAAGCCCTAG TGCCTCTGCC        60

GGCTGCCCAG GACCTGGTAT CGGCCCACAG ACCAAGTCCT CCACAGAGGG CGAGCCAGGG       120

TGGAGAAGAG CCAGCCCAGT GACCCAAACA TCCCCGATAA ACACCCACT  GCTTAAGAGG       180

CAGGCTCGG ATG GAC TAT AGC TTT GAT ACC ACA GCC GAA GAC CCT TGG           228
```

```
                Met Asp Tyr Ser Phe Asp Thr Thr Ala Glu Asp Pro Trp
                 1               5                  10

GTT AGG ATT TCT GAC TGC ATC AAA AAC TTA TTT AGC CCC ATC ATG AGT        276
Val Arg Ile Ser Asp Cys Ile Lys Asn Leu Phe Ser Pro Ile Met Ser
     15                  20                  25

GAG AAC CAT GGC CAC ATG CCT CTA CAG CCC AAT GCC AGC CTG AAT GAA        324
Glu Asn His Gly His Met Pro Leu Gln Pro Asn Ala Ser Leu Asn Glu
 30                  35                  40                  45

GAA GAA GGG ACA CAG GGC CAC CCA GAT GGG ACC CCA CCA AAG CTG GAC        372
Glu Glu Gly Thr Gln Gly His Pro Asp Gly Thr Pro Pro Lys Leu Asp
             50                  55                  60

ACC GCC AAT GGC ACT CCC AAA GTT TAC AAG TCA GCA GAC AGC AGC ACT        420
Thr Ala Asn Gly Thr Pro Lys Val Tyr Lys Ser Ala Asp Ser Ser Thr
                 65                  70                  75

GTG AAG AAA GGT CCT CCT GTG GCT CCC AAG CCA GCC TGG TTT CGC CAA        468
Val Lys Lys Gly Pro Pro Val Ala Pro Lys Pro Ala Trp Phe Arg Gln
         80                  85                  90

AGC TTG AAA GGT TTG AGG AAT CGT GCT TCA GAC CCA AGA GGG CTC CCT        516
Ser Leu Lys Gly Leu Arg Asn Arg Ala Ser Asp Pro Arg Gly Leu Pro
     95                 100                 105

GAT CCT GCC TTG TCC ACC CAG CCA GCA CCT GCT TCC AGG GAG CAC CTA        564
Asp Pro Ala Leu Ser Thr Gln Pro Ala Pro Ala Ser Arg Glu His Leu
110                 115                 120                 125

GGA TCA CAC ATC CGG GCC TCC TCC TCC TCC TCC TCC ATC AGG CAG AGA        612
Gly Ser His Ile Arg Ala Ser Ser Ser Ser Ser Ser Ile Arg Gln Arg
                130                 135                 140

ATC AGC TCC TTT GAA ACC TTT GGC TCC TCT CAA CTG CCT GAC AAA GGA        660
Ile Ser Ser Phe Glu Thr Phe Gly Ser Ser Gln Leu Pro Asp Lys Gly
                145                 150                 155

GCC CAG AGA CTG AGC CTC CAG CCC TCC TCT GGG GAG GCA GCA AAA CCT        708
Ala Gln Arg Leu Ser Leu Gln Pro Ser Ser Gly Glu Ala Ala Lys Pro
            160                 165                 170

CTT GGG AAG CAT GAG GAA GGA CGG TTT TCT GGA CTC TTG GGG CGA GGG        756
Leu Gly Lys His Glu Glu Gly Arg Phe Ser Gly Leu Leu Gly Arg Gly
        175                 180                 185

GCT GCA CCC ACT CTT GTG CCC CAG CAG CCT GAG CAA GTA CTG TCC TCG        804
Ala Ala Pro Thr Leu Val Pro Gln Gln Pro Glu Gln Val Leu Ser Ser
190                 195                 200                 205

GGG TCC CCT GCA GCC TCC GAG GCC AGA GAC CCA GGC GTG TCT GAG TCC        852
Gly Ser Pro Ala Ala Ser Glu Ala Arg Asp Pro Gly Val Ser Glu Ser
                210                 215                 220

CCT CCC CCA GGG CGG CAG CCC AAT CAG AAA ACT CTC CCC CCT GGC CCG        900
Pro Pro Pro Gly Arg Gln Pro Asn Gln Lys Thr Leu Pro Pro Gly Pro
                225                 230                 235

GAC CCG CTC CTA AGG CTG CTG TCA ACA CAG GCT GAG GAA TCT CAA GGC        948
Asp Pro Leu Leu Arg Leu Leu Ser Thr Gln Ala Glu Glu Ser Gln Gly
            240                 245                 250

CCA GTG CTC AAG ATG CCT AGC CAG CGA GCA CGG AGC TTC CCC CTG ACC        996
Pro Val Leu Lys Met Pro Ser Gln Arg Ala Arg Ser Phe Pro Leu Thr
        255                 260                 265

AGG TCC CAG TCC TGT GAG ACG AAG CTA CTT GAC GAA AAG ACC AGC AAA       1044
Arg Ser Gln Ser Cys Glu Thr Lys Leu Leu Asp Glu Lys Thr Ser Lys
270                 275                 280                 285

CTC TAT TCT ATC AGC AGC CAA GTG TCA TCG GCT GTC ATG AAA TCC TTG       1092
Leu Tyr Ser Ile Ser Ser Gln Val Ser Ser Ala Val Met Lys Ser Leu
                290                 295                 300

CTG TGC CTT CCA TCT TCT ATC TCC TGT GCC CAG ACT CCC TGC ATC CCC       1140
Leu Cys Leu Pro Ser Ser Ile Ser Cys Ala Gln Thr Pro Cys Ile Pro
                305                 310                 315
```

```
AAG GAA GGG GCA TCT CCA ACA TCA TCA TCC AAC GAA GAC TCA GCT GCA      1188
Lys Glu Gly Ala Ser Pro Thr Ser Ser Ser Asn Glu Asp Ser Ala Ala
            320                 325                 330

AAT GGT TCT GCT GAA ACA TCT GCC TTG GAC ACA GGG TTC TCG CTC AAC      1236
Asn Gly Ser Ala Glu Thr Ser Ala Leu Asp Thr Gly Phe Ser Leu Asn
    335                 340                 345

CTT TCA GAG CTG AGA GAA TAT ACA GAG GGT CTC ACG GAA GCC AAG GAA      1284
Leu Ser Glu Leu Arg Glu Tyr Thr Glu Gly Leu Thr Glu Ala Lys Glu
350                 355                 360                 365

GAC GAT GAT GGG GAC CAC AGT TCC CTT CAG TCT GGT CAG TCC GTT ATC      1332
Asp Asp Asp Gly Asp His Ser Ser Leu Gln Ser Gly Gln Ser Val Ile
                370                 375                 380

TCC CTG CTG AGC TCA GAA GAA TTA AAA AAA CTC ATC GAG GAG GTG AAG      1380
Ser Leu Leu Ser Ser Glu Glu Leu Lys Lys Leu Ile Glu Glu Val Lys
            385                 390                 395

GTT CTG GAT GAA GCA ACA TTA AAG CAA TTA GAC GGC ATC CAT GTC ACC      1428
Val Leu Asp Glu Ala Thr Leu Lys Gln Leu Asp Gly Ile His Val Thr
        400                 405                 410

ATC TTA CAC AAG GAG GAA GGT GCT GGT CTT GGG TTC AGC TTG GCA GGA      1476
Ile Leu His Lys Glu Glu Gly Ala Gly Leu Gly Phe Ser Leu Ala Gly
    415                 420                 425

GGA GCA GAT CTA GAA AAC AAG GTG ATT ACG GTT CAC AGA GTG TTT CCA      1524
Gly Ala Asp Leu Glu Asn Lys Val Ile Thr Val His Arg Val Phe Pro
430                 435                 440                 445

AAT GGG CTG GCC TCC CAG GAA GGG ACT ATT CAG AAG GGC AAT GAG GTT      1572
Asn Gly Leu Ala Ser Gln Glu Gly Thr Ile Gln Lys Gly Asn Glu Val
                450                 455                 460

CTT TCC ATC AAC GGC AAG TCT CTC AAG GGG ACC ACG CAC CAT GAT GCC      1620
Leu Ser Ile Asn Gly Lys Ser Leu Lys Gly Thr Thr His His Asp Ala
            465                 470                 475

TTG GCA ATC CTC CGC CAA GCT CGA GAG CCC AGG CAA GCT GTG ATT GTC      1668
Leu Ala Ile Leu Arg Gln Ala Arg Glu Pro Arg Gln Ala Val Ile Val
        480                 485                 490

ACA AGG AAG CTG ACT CCA GAG GCC ATG CCC GAC CTC AAC TCC TCC ACT      1716
Thr Arg Lys Leu Thr Pro Glu Ala Met Pro Asp Leu Asn Ser Ser Thr
    495                 500                 505

GAC TCT GCA GCC TCA GCC TCT GCA GCC AGT GAT GTT TCT GTA GAA TCT      1764
Asp Ser Ala Ala Ser Ala Ser Ala Ala Ser Asp Val Ser Val Glu Ser
510                 515                 520                 525

ACA GCA GAG GCC ACA GTC TGC ACG GTG ACA CTG GAG AAG ATG TCG GCA      1812
Thr Ala Glu Ala Thr Val Cys Thr Val Thr Leu Glu Lys Met Ser Ala
                530                 535                 540

GGG CTG GGC TTC AGC CTG GAA GGA GGG AAG GGC TCC CTA CAC GGA GAC      1860
Gly Leu Gly Phe Ser Leu Glu Gly Gly Lys Gly Ser Leu His Gly Asp
            545                 550                 555

AAG CCT CTC ACC ATT AAC AGG ATT TTC AAA GGA GCA GCC TCA GAA CAA      1908
Lys Pro Leu Thr Ile Asn Arg Ile Phe Lys Gly Ala Ala Ser Glu Gln
        560                 565                 570

AGT GAG ACA GTC CAG CCT GGA GAT GAA ATC TTG CAG CTG GGT GGC ACT      1956
Ser Glu Thr Val Gln Pro Gly Asp Glu Ile Leu Gln Leu Gly Gly Thr
    575                 580                 585

GCC ATG CAG GGC CTC ACA CGG TTT GAA GCC TGG AAC ATC ATC AAG GCA      2004
Ala Met Gln Gly Leu Thr Arg Phe Glu Ala Trp Asn Ile Ile Lys Ala
590                 595                 600                 605

CTG CCT GAT GGA CCT GTC ACG ATT GTC ATC AGG AGA AAA AGC CTC CAG      2052
Leu Pro Asp Gly Pro Val Thr Ile Val Ile Arg Arg Lys Ser Leu Gln
                610                 615                 620

TCC AAG GAA ACC ACA GCT GCT GGA GAC TCC TAG GCAGGACATG CTGAAGCCAA    2105
Ser Lys Glu Thr Thr Ala Ala Gly Asp Ser  *
            625                 630
```

-continued

```
AGCCAATAAC ACACAGCTAA CACACAGCTC CCATAACCGC TGATTCTCAG GGTCTCTGCT    2165

GCCGCCCCAC CCAGATGGGG GAAAGCACAG GTGGGCTTCC CAGTGGCTGC TGCCCAGGCC    2225

CAGACCTTCT AGGACGCCAC CCAGCAAAAG GTTGTTCCTA AAATAAGGGC AGAGTCACAC    2285

GGGGGCAGCT GATACAAATT GCAGACTGTG TAAAAAGAGA GCTTAATGAT AATATTGTGG    2345

TGCCACAAAT AAAATGGATT TATTAGAATT TCATATGACA TTCATGCCTG GCTTCGCAAA    2405

ATGTTTCAAG TACTGTAACT GTGTCATGAT TCACCCCCAA ACAGTGACAT TTATTTTTCT    2465

CATGAATCTG CAATGTGGGC AGAGATTGGA ATGGGCAGCT CATCTCTGTC CCACTTGGCA    2525

TCAGCTGGCG TCATGCAAAG TCATGCAAAG GCTGGGACCA CGTGAGATCA TTCACTCATA    2585

CATCTGGCCG TTGATGTTGG CTGGGAACTC ACCTGGGGCT GCTGGCCTGA ATGCTTATAG    2645

GTGGCCTCTC CTTGTGGCCT GGCCTCCTCA CAACATGGTG TCTGGATTCC CAGGATGAGC    2705

ATCCCAGGAT CGCAAGAGCC ACGTAGAAGC TGCATCTTGT TTATACCTTT GCCTTGGAAG    2765

TTGCATGGCA TCACCTCCAC CATACTCCAT CAGTTAGAGC TGACACAAAC CTGCCTGGGT    2825

TTAAGGGGAG AGGAAATATT GCTGGGGTCA TTTATGAAAA ATACAGTTTG TCACATGAAA    2885

CATTTGCAAA ATTGTTTTTG GTTGGATTGG AGAAGTAATC CTAGGGAAGG GTGGTGGAGC    2945

CAGTAAACAG AGGAGTACAG GTGAAGCACC AAGCTCAAAG CGTGGACAGG TGTGCCGACA    3005

GAAGGAACCA GCGTGTATAT GAGGGTATCA AATAAAATTG CTACTACTTA CCTACC        3061
```

(2) INFORMATION FOR SEQ ID NO: 7:

(i) SEQUENCE CHARACTERISTICS:
        (A) LENGTH: 631 amino acids
        (B) TYPE: amino acid
        (D) TOPOLOGY: linear (ii) MOLECULE TYPE: protein (xi) SEQUENCE DESCRIPTION: SEQ ID NO: 7:

```
Met Asp Tyr Ser Phe Asp Thr Thr Ala Glu Asp Pro Trp Val Arg Ile
 1               5                  10                  15

Ser Asp Cys Ile Lys Asn Leu Phe Ser Pro Ile Met Ser Glu Asn His
                20                  25                  30

Gly His Met Pro Leu Gln Pro Asn Ala Ser Leu Asn Glu Glu Gly
            35                  40                  45

Thr Gln Gly His Pro Asp Gly Thr Pro Pro Lys Leu Asp Thr Ala Asn
    50                  55                  60

Gly Thr Pro Lys Val Tyr Lys Ser Ala Asp Ser Ser Thr Val Lys Lys
65                  70                  75                  80

Gly Pro Pro Val Ala Pro Lys Pro Ala Trp Phe Arg Gln Ser Leu Lys
                85                  90                  95

Gly Leu Arg Asn Arg Ala Ser Asp Pro Arg Gly Leu Pro Asp Pro Ala
            100                 105                 110

Leu Ser Thr Gln Pro Ala Pro Ala Ser Arg Glu His Leu Gly Ser His
        115                 120                 125

Ile Arg Ala Ser Ser Ser Ser Ser Ile Arg Gln Arg Ile Ser Ser
    130                 135                 140

Phe Glu Thr Phe Gly Ser Ser Gln Leu Pro Asp Lys Gly Ala Gln Arg
145                 150                 155                 160

Leu Ser Leu Gln Pro Ser Ser Gly Glu Ala Ala Lys Pro Leu Gly Lys
                165                 170                 175

His Glu Glu Gly Arg Phe Ser Gly Leu Leu Gly Arg Gly Ala Ala Pro
```

-continued

```
                180             185             190
Thr Leu Val Pro Gln Pro Glu Gln Val Leu Ser Ser Gly Ser Pro
            195             200             205
Ala Ala Ser Glu Ala Arg Asp Pro Gly Val Ser Glu Ser Pro Pro Pro
210                 215             220
Gly Arg Gln Pro Asn Gln Lys Thr Leu Pro Pro Gly Pro Asp Pro Leu
225             230              235                     240
Leu Arg Leu Leu Ser Thr Gln Ala Glu Glu Ser Gln Gly Pro Val Leu
                245             250             255
Lys Met Pro Ser Gln Arg Ala Arg Ser Phe Pro Leu Thr Arg Ser Gln
            260             265             270
Ser Cys Glu Thr Lys Leu Leu Asp Glu Lys Thr Ser Lys Leu Tyr Ser
            275             280             285
Ile Ser Ser Gln Val Ser Ser Ala Val Met Lys Ser Leu Leu Cys Leu
            290             295             300
Pro Ser Ser Ile Ser Cys Ala Gln Thr Pro Cys Ile Pro Lys Glu Gly
305             310             315             320
Ala Ser Pro Thr Ser Ser Ser Asn Glu Asp Ser Ala Ala Asn Gly Ser
                325             330             335
Ala Glu Thr Ser Ala Leu Asp Thr Gly Phe Ser Leu Asn Leu Ser Glu
            340             345             350
Leu Arg Glu Tyr Thr Glu Gly Leu Thr Glu Ala Lys Glu Asp Asp Asp
                355             360             365
Gly Asp His Ser Ser Leu Gln Ser Gly Gln Ser Val Ile Ser Leu Leu
            370             375             380
Ser Ser Glu Glu Leu Lys Lys Leu Ile Glu Glu Val Lys Val Leu Asp
385             390             395             400
Glu Ala Thr Leu Lys Gln Leu Asp Gly Ile His Val Thr Ile Leu His
                405             410             415
Lys Glu Glu Gly Ala Gly Leu Gly Phe Ser Leu Ala Gly Gly Ala Asp
                420             425             430
Leu Glu Asn Lys Val Ile Thr Val His Arg Val Phe Pro Asn Gly Leu
            435             440             445
Ala Ser Gln Glu Gly Thr Ile Gln Lys Gly Asn Glu Val Leu Ser Ile
450             455             460
Asn Gly Lys Ser Leu Lys Gly Thr Thr His His Asp Ala Leu Ala Ile
465             470             475             480
Leu Arg Gln Ala Arg Glu Pro Arg Gln Ala Val Ile Val Thr Arg Lys
                485             490             495
Leu Thr Pro Glu Ala Met Pro Asp Leu Asn Ser Ser Thr Asp Ser Ala
            500             505             510
Ala Ser Ala Ser Ala Ala Ser Asp Val Ser Val Glu Ser Thr Ala Glu
            515             520             525
Ala Thr Val Cys Thr Val Thr Leu Glu Lys Met Ser Ala Gly Leu Gly
            530             535             540
Phe Ser Leu Glu Gly Gly Lys Gly Ser Leu His Gly Asp Lys Pro Leu
545             550             555             560
Thr Ile Asn Arg Ile Phe Lys Gly Ala Ala Ser Glu Gln Ser Glu Thr
                565             570             575
Val Gln Pro Gly Asp Glu Ile Leu Gln Leu Gly Gly Thr Ala Met Gln
            580             585             590
Gly Leu Thr Arg Phe Glu Ala Trp Asn Ile Ile Lys Ala Leu Pro Asp
            595             600             605
```

-continued

```
Gly Pro Val Thr Ile Val Ile Arg Arg Lys Ser Leu Gln Ser Lys Glu
    610                 615                 620
Thr Thr Ala Ala Gly Asp Ser
625                 630
```